United States Patent
Prud'homme et al.

(10) Patent No.: US 12,357,582 B2
(45) Date of Patent: Jul. 15, 2025

(54) HYDROPHOBIC ION PAIRING AND FLASH NANOPRECIPITATION FOR FORMATION OF CONTROLLED-RELEASE NANOCARRIER FORMULATIONS

(71) Applicant: The Trustees of Princeton University, Princeton, NJ (US)

(72) Inventors: Robert K. Prud'homme, Princeton, NJ (US); Kurt D. Ristroph, Princeton, NJ (US); Nathalie M. Pinkerton, Princeton, NJ (US); Hoang D. Lu, Princeton, NJ (US); Paradorn Rummaneethorn, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 16/761,140

(22) PCT Filed: Nov. 2, 2018

(86) PCT No.: PCT/US2018/058869
§ 371 (c)(1),
(2) Date: May 1, 2020

(87) PCT Pub. No.: WO2019/090030
PCT Pub. Date: May 9, 2019

(65) Prior Publication Data
US 2020/0268679 A1    Aug. 27, 2020

Related U.S. Application Data

(60) Provisional application No. 62/581,394, filed on Nov. 3, 2017.

(51) Int. Cl.
*A61K 9/51*        (2006.01)
*A61K 31/5377*    (2006.01)
(Continued)

(52) U.S. Cl.
CPC .......... *A61K 9/5153* (2013.01); *A61K 9/5161* (2013.01); *A61K 9/5192* (2013.01);
(Continued)

(58) Field of Classification Search
CPC .. A61K 9/5153; A61K 9/5161; A61K 9/5192; A61K 31/5377; A61K 31/7036;
(Continued)

(56) References Cited

U.S. PATENT DOCUMENTS

| | | | |
|---|---|---|---|
| 1,690,760 | A | 11/1928 | Volwiler |
| 4,342,653 | A | 8/1982 | Halverson |

(Continued)

FOREIGN PATENT DOCUMENTS

| | | |
|---|---|---|
| CN | 100389766 C | 5/2008 |
| CN | 102334609 A | 2/2012 |

(Continued)

OTHER PUBLICATIONS

Tang, C., et al in Europian Jouranl of Pharmaceutical Sciences, vol. 102, pp. 63-70, 2017.*

(Continued)

*Primary Examiner* — Isaac Shomer
(74) *Attorney, Agent, or Firm* — Nixon & Vanderhye P.C.; Lars H. Genieser

(57) ABSTRACT

Methods for encapsulating water-soluble biologic and small molecule active pharmaceutical ingredients (APIs) into nanoparticles by applying nanoprecipitation techniques and ion-pairing the nanoparticles with hydrophobic counterions to produce new API salts that exhibit altered solubilities are presented.

16 Claims, 10 Drawing Sheets

Specification includes a Sequence Listing.

(51) Int. Cl.
  *A61K 31/7036* (2006.01)
  *A61K 38/10* (2006.01)
  *A61K 38/12* (2006.01)
  *A61K 38/38* (2006.01)
  *A61K 38/47* (2006.01)

(52) U.S. Cl.
  CPC ...... *A61K 31/5377* (2013.01); *A61K 31/7036* (2013.01); *A61K 38/10* (2013.01); *A61K 38/12* (2013.01); *A61K 38/38* (2013.01); *A61K 38/47* (2013.01)

(58) Field of Classification Search
  CPC ........ A61K 38/10; A61K 38/12; A61K 38/38; A61K 38/47; A61K 9/5146; A61K 47/541; A61K 47/6929; A61P 31/04; C12Y 302/01017
  See application file for complete search history.

(56) References Cited

U.S. PATENT DOCUMENTS

| | | | |
|---|---|---|---|
| 4,382,982 A | 5/1983 | Whillans | |
| 4,678,516 A | 7/1987 | Alderman et al. | |
| 4,695,464 A | 9/1987 | Alderman | |
| 4,888,238 A | 12/1989 | Katz et al. | |
| 4,999,417 A | 3/1991 | Domb | |
| 5,366,734 A | 11/1994 | Hutchinson | |
| 5,383,500 A | 1/1995 | Dwars et al. | |
| 5,578,325 A | 11/1996 | Domb et al. | |
| 5,851,579 A | 12/1998 | Wu et al. | |
| 6,291,013 B1 | 9/2001 | Gibson | |
| 6,383,500 B1 | 5/2002 | Wooley et al. | |
| 6,610,653 B1 | 8/2003 | Backstrom et al. | |
| 6,730,322 B1 | 5/2004 | Bernstein et al. | |
| 6,998,426 B2 | 2/2006 | L'Alloret | |
| 7,052,719 B2 | 5/2006 | Bernstein | |
| 7,842,308 B2 | 11/2010 | McAllister et al. | |
| 7,977,024 B2 | 7/2011 | Zhou et al. | |
| 8,137,699 B2 | 3/2012 | Johnson et al. | |
| 8,288,001 B1 | 10/2012 | Fan et al. | |
| 8,298,581 B2 | 10/2012 | Fischer et al. | |
| 8,603,514 B2 | 12/2013 | Yang | |
| 8,623,329 B1 | 1/2014 | Hansen et al. | |
| 8,703,196 B2 | 4/2014 | Babcock et al. | |
| 9,504,658 B2 | 11/2016 | Miller et al. | |
| 9,603,830 B2 | 3/2017 | Powell | |
| 9,782,358 B2 | 10/2017 | Kataoka et al. | |
| 10,231,937 B2 | 3/2019 | Pagels et al. | |
| 11,103,461 B2 | 8/2021 | Prud'Homme et al. | |
| 2004/0023393 A1 | 2/2004 | Monahan et al. | |
| 2004/0052824 A1 | 3/2004 | Chacra-Vernet | |
| 2004/0091546 A1 | 5/2004 | Johnson et al. | |
| 2004/0236050 A1 | 11/2004 | Lundquist et al. | |
| 2005/0158390 A1 | 7/2005 | Rana et al. | |
| 2005/0228074 A1 | 10/2005 | Warren et al. | |
| 2006/0040831 A1* | 2/2006 | Cassidy | C23F 11/141 507/245 |
| 2006/0057215 A1 | 3/2006 | Raiche et al. | |
| 2006/0078624 A1 | 4/2006 | Zalipsky et al. | |
| 2006/0159921 A1 | 7/2006 | Murthy et al. | |
| 2006/0224095 A1 | 10/2006 | Claverie et al. | |
| 2006/0247383 A1 | 11/2006 | Hedrick et al. | |
| 2007/0042498 A1* | 2/2007 | Ebner | G01N 33/68 436/128 |
| 2007/0231355 A1 | 10/2007 | Quadir et al. | |
| 2008/0145432 A1 | 6/2008 | Kakizawa et al. | |
| 2008/0160305 A1 | 7/2008 | Warren et al. | |
| 2008/0274194 A1 | 11/2008 | Miller et al. | |
| 2009/0061009 A1 | 3/2009 | Schwarz et al. | |
| 2009/0068743 A1 | 3/2009 | Turnell et al. | |
| 2009/0155326 A1* | 6/2009 | Mack | A61K 31/4164 514/230.2 |
| 2009/0325292 A1 | 12/2009 | Baker et al. | |
| 2010/0150994 A1 | 6/2010 | Kotyla | |
| 2010/0166866 A1 | 7/2010 | Fischer et al. | |
| 2010/0203149 A1* | 8/2010 | Radosz | A61P 35/00 424/490 |
| 2010/0233251 A1 | 9/2010 | Von Andrian et al. | |
| 2010/0305219 A1 | 12/2010 | Granick et al. | |
| 2010/0310649 A1 | 12/2010 | Richard et al. | |
| 2010/0330368 A1 | 12/2010 | Prud'homme et al. | |
| 2011/0012057 A1 | 1/2011 | Lindner et al. | |
| 2011/0022129 A1* | 1/2011 | Prud'homme | A61K 9/0009 977/773 |
| 2011/0064821 A1* | 3/2011 | Catchpole | A61K 9/1647 977/773 |
| 2011/0200828 A1 | 8/2011 | Li et al. | |
| 2011/0206739 A1 | 8/2011 | Nicolosi et al. | |
| 2011/0229516 A1 | 9/2011 | Ochomogo et al. | |
| 2011/0236686 A1 | 9/2011 | Kitano et al. | |
| 2011/0293701 A1 | 12/2011 | Bratzler et al. | |
| 2012/0009267 A1 | 1/2012 | Cho et al. | |
| 2012/0041150 A1 | 2/2012 | Yabu et al. | |
| 2012/0121510 A1* | 5/2012 | Brem | A61K 31/337 424/9.1 |
| 2012/0171254 A1 | 7/2012 | Johnson et al. | |
| 2012/0230913 A1 | 9/2012 | Johnston et al. | |
| 2012/0308640 A1 | 12/2012 | Percec et al. | |
| 2013/0064954 A1 | 3/2013 | Ochomogo et al. | |
| 2013/0101516 A1 | 4/2013 | Zhao | |
| 2013/0115272 A1 | 5/2013 | De Fougerolles et al. | |
| 2013/0122058 A1 | 5/2013 | Chow et al. | |
| 2013/0171208 A1 | 7/2013 | Smith et al. | |
| 2013/0337078 A1 | 12/2013 | Mayer et al. | |
| 2014/0037573 A1 | 2/2014 | Eliasof et al. | |
| 2014/0099379 A1 | 4/2014 | Beck-Broichsitter et al. | |
| 2014/0249235 A1 | 9/2014 | Brugel et al. | |
| 2014/0302154 A1 | 10/2014 | Waldoefner et al. | |
| 2014/0356443 A1 | 12/2014 | Brisander et al. | |
| 2015/0086618 A1* | 3/2015 | Onyuksel | A61K 38/26 514/1.5 |
| 2015/0218198 A1 | 8/2015 | Petermann et al. | |
| 2015/0283218 A1 | 10/2015 | Shea et al. | |
| 2015/0290233 A1 | 10/2015 | Yarden et al. | |
| 2015/0298084 A1 | 10/2015 | Schoeppe et al. | |
| 2015/0299369 A1 | 10/2015 | Ausserre et al. | |
| 2016/0235677 A1 | 8/2016 | Hoerr et al. | |
| 2016/0317459 A1 | 11/2016 | Ensign et al. | |
| 2016/0346266 A1 | 12/2016 | Tolleth et al. | |
| 2017/0042823 A1 | 2/2017 | Prud'homme et al. | |
| 2017/0151339 A1* | 6/2017 | White | A61P 35/00 |
| 2017/0209386 A1 | 7/2017 | Pagels et al. | |
| 2018/0009924 A1 | 1/2018 | Sadowski et al. | |
| 2018/0125915 A1 | 5/2018 | Mikhail | |
| 2019/0008788 A1 | 1/2019 | Prud'Homme et al. | |
| 2019/0151252 A1 | 5/2019 | Pagels et al. | |
| 2019/0192444 A1 | 6/2019 | Barzilay et al. | |
| 2020/0023332 A1 | 1/2020 | Prud'homme et al. | |
| 2020/0147032 A1 | 5/2020 | Prud'homme et al. | |
| 2020/0206136 A1 | 7/2020 | Prud'homme et al. | |
| 2021/0085619 A1 | 3/2021 | Baldwin et al. | |
| 2021/0378980 A1 | 12/2021 | Horhota et al. | |
| 2021/0379181 A1 | 12/2021 | Rauch et al. | |

FOREIGN PATENT DOCUMENTS

| | | |
|---|---|---|
| CN | 104042567 A | 9/2014 |
| CN | 105213250 A | 1/2016 |
| CN | 106750272 A | 5/2017 |
| EP | 2962752 A1 | 1/2016 |
| JP | 2000514791 A | 11/2000 |
| JP | 2003513019 A | 4/2003 |
| JP | 2008297288 A | 12/2008 |
| JP | 2011506499 A | 3/2011 |
| JP | 2014514275 A | 6/2014 |
| JP | 2015129128 A | 7/2015 |
| JP | 2015529683 A | 10/2015 |
| JP | 2017505800 A | 2/2017 |
| JP | 2018535228 A | 11/2018 |
| WO | 94/08599 * | 4/1994 |
| WO | WO 1997049387 A1 | 12/1997 |
| WO | WO 1997049736 A2 | 12/1997 |

(56) References Cited

FOREIGN PATENT DOCUMENTS

| | | | |
|---|---|---|---|
| WO | WO 2001022937 A1 | 4/2001 | |
| WO | WO 2002076441 A1 | 10/2002 | |
| WO | WO 2002078674 A1 | 10/2002 | |
| WO | WO 2002092069 A1 | 11/2002 | |
| WO | WO 2009080164 A1 | 7/2009 | |
| WO | WO 2010148653 A1 | 12/2010 | |
| WO | WO 2012122544 A2 | 9/2012 | |
| WO | WO 2013023003 A1 | 2/2013 | |
| WO | WO 2013160773 A2 | 10/2013 | |
| WO | WO 2014043625 A1 | 3/2014 | |
| WO | WO 2014133172 A1 | 9/2014 | |
| WO | WO 2014165679 A1 | 10/2014 | |
| WO | WO 2015123562 A1 | 8/2015 | |
| WO | WO 2015130835 A1 | 9/2015 | |
| WO | WO 2015200054 A2 | 12/2015 | |
| WO | WO 2015200054 A9 | 12/2015 | |
| WO | WO 2016193810 A1 | 12/2016 | |
| WO | 2017/089942 | * | 6/2017 |
| WO | WO 2017089942 A1 | 6/2017 | |
| WO | WO 2017112828 A1 | 6/2017 | |
| WO | WO 2017/130046 A1 | 8/2017 | |
| WO | WO 2019/050969 A1 | 3/2019 | |
| WO | WO 2019055539 A1 | 3/2019 | |
| WO | WO 2019090030 A1 | 5/2019 | |
| WO | WO 2020018890 A1 | 1/2020 | |
| WO | WO 2020/227350 A1 | 11/2020 | |
| WO | WO 2020252346 A1 | 12/2020 | |
| WO | WO 2021/046078 A1 | 3/2021 | |

OTHER PUBLICATIONS

Patel et al Jouranl of Microencapsulation, vol. 31 (6), pp. 542-555-, 2014.*
Tian Zhou et al. "PEG-b-PCL polymeric nano-micelle inhibits vascular angiogenesis by activating p53-dependent apoptosis in zebrafish." International Journal of Nanomedicine, vol. 11, 2016, pp. 6517-6531. (Year: 2016).*
Ricardo A. de Azevedo et al. "Mastoparan induces apoptosis in B16F10-Nex2 melanoma cells via the intrinsic mitochondrial pathway and displays antitumor activity in vivo." Peptides, vol. 68, 2015, pp. 113-119. (Year: 2015).*
Isabel Gessner and Ines Neundorf. "Nanoparticles Modified with Cell-Penetrating Peptides: Conjugation Mechanisms, Physicochemical Properties, and Application in Cancer Diagnosis and Therapy." International Journal of Molecular Sciences, vol. 21, 2020, 2536, pp. 1-21. (Year: 2020).*
Young Ho Song et al. "A novel in situ hydrophobic ion pairing (HIP) formulation strategy for clinical product selection of a nanoparticle drug delivery system." Journal of Controlled Release, vol. 229, 2016, pp. 106-119. (Year: 2016).*
Seung Ho Choi and Tae Gwan Park. "Hydrophobic ion pair formation between leuprolide and sodium oleate for sustained release from biodegradable polymeric microspheres." International Journal of Pharmaceutics, vol. 203 (2000), pp. 193-202. (Year: 2000).*
U.S. Appl. No. 18/083,458 Restriction/Election Requirement dated Aug. 1, 2024.
Xu et al., "Influence of experimental parameters and the copolymer structure on the size control of nanospheres in double emulsion method", J. Polymer Research, vol. 18, pp. 131-137 (2011).
U.S. Appl. No. 17/260,640 Notice of Allowance & Notice of Allowability dated Aug. 16, 2024.
International Patent Application PCT/US2018/050714 International Search Report and Written Opinion dated Dec. 6, 2018.
International Patent Application PCT/US2018/058869 International Search Report and Written Opinion dated Feb. 22, 2019.
International Patent Application PCT/US2019/042574 International Search Report and Written Opinion dated Nov. 22, 2019.
International Patent Application PCT/US2020/031579 International Search Report and Written Opinion dated Aug. 3, 2020.
International Patent Application PCT/US2020/037542 International Search Report and Written Opinion dated Sep. 11, 2020.
International Patent Application PCT/US2020/048986 International Search Report and Written Opinion dated Feb. 16, 2021.
IQQueryQuickExport search results—202004301516 (IP.com NPL search results)—downloaded Apr. 30, 2020, 4 pages.
IQQueryQuickExport search results—202004301547 (IP.com NPL search results)—downloaded Apr. 30, 2020, 2 pages.
IQQueryQuickExport search results—202004301605 (IP.com NPL search results)—downloaded Apr. 30, 2020, 5 pages.
IQQueryQuickExport search results—202004301643 (IP.com NPL search results)—downloaded Apr. 30, 2020, 5 pages.
IQQueryQuickExport search results—202004301659 (IP.com NPL search results)—downloaded Apr. 30, 2020, 5 pages.
QQueryQuickExport search results—202004301700 (IP.com NPL search results)—downloaded Apr. 30, 2020, 2 pages.
Jain et al., "Peptide and Protein Delivery Using New Drug Delivery Systems", Crit. Revs. Ther. Drug Carrier Syst., vol. 30, No. 4, pp. 293-329 (2013).
Jang et al., "Bicontinuous Block Copolymer Morphologies Produced by Interfacially Active, Thermally Stable Nanoparticles", Macromols., vol. 44, pp. 9366-9373 (2011).
Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/cism05223c.
Jeon et al., "Cooperative Assembly of Block Copolymers with Deformable Interfaces: Toward Nanostructured Particles", Advanced Materials, vol. 20, pp. 4103-4108 (2008), doi: 10.1002/adma. 200801377.
Johnson et al., "Characterization and Suitability of Therapeutic Antibody Dense Phases for Subcutaneous Delivery", Molecular Pharmaceutics, vol. 10, pp. 3582-3591 (2013).
Johnson et al., "Chemical Processing and Micromixing in Confined Impinging Jets", AIChE Journal, vol. 49, No. 9, pp. 2264-2282 (2003).
Johnson et al., "Flash NanoPrecipitation of Organic Actives and Block Copolymers using a Confined Impinging Jets Mixer", Australian Journal of Chemistry, vol. 56, No. 10, pp. 1021-1024 (2003).
Johnson et al., "Nanoprecipitation of Organic Actives Using Mixing and Block Copolymer Stabilization", Abstracts of Papers of the American Chemical Society, No. 186 (Abstract) (Sep. 2003).
Johnson et al., "Engineering the Direct Precipitation of Stabilized Organic and Block Copolymer Nonparticles as Unique Composites", Abstracts of Papers of the American Chemical Society, No. 441 (Abstract) (Sep. 2003).
Johnston et al., "Concentrated Dispersions of Equilibrium Protein Nanoclusters That Reversibly Dissociate into Active Monomers", ACS Nano, vol. 6, No. 2, pp. 1357-1369 (2012).
Kakizawa et al., "Controlled release of protein drugs from newly developed amphiphilic polymer-based microparticles composed of nanoparticles", Journal of Controlled Release, vol. 142, pp. 8-13 (2010).
Kang et al., "Pore Closing and Opening in Biodegradable Polymers and Their Effect on the Controlled Release of Proteins", Mol. Pharmaceutics, vol. 4, No. 1, pp. 104-118 (2007).
Khanvilkar et al., "Drug transfer through mucus", Advanced Drug Delivery Reviews, vol. 48, Nos. 2-3, pp. 173-193 (2001).
Kim et al., "Critical effect of freezing/freeze-drying on sustained release of FITC-dextran encapsulated within PLGA microspheres", Int'l J. Pharmaceutics, vol. 271, pp. 207-214 (2004).
Kim et al., "Multicomponent Nanoparticles via Self-Assembly with Cross-Linked Block Copolymer Surfactants", Langmuir, vol. 23, pp. 2198-2202 (2007).
Kohen, N., "Characterization of Polystyrene-block-poly(acrylic acid) Micelles In Solution and Assembled on Solid Substrates", Massachusetts Institute of Technology, Thesis, pp. 1-38 (Jun. 2005).
Kovalainen et al., "Novel Delivery Systems for Improving the Clinical Use of Peptides", Pharmacol. Rev., vol. 67, No. 3, pp. 541-561 (Jul. 2015).
Kumar et al., "Amphiphilic Janus particles at fluid interfaces", Soft Matter, vol. 9, pp. 6604-6617 (2013).

(56) References Cited

OTHER PUBLICATIONS

Lai et al., "Mucus-penetrating nanoparticles for drug and gene delivery to mucosal tissues", Advanced Drug Delivery Reviews, vol. 61, No. 2, pp. 158-171 (2009).
Lai et al., "Rapid transport of large polymeric nanoparticles in fresh undiluted human mucus", Proceedings National Academy of Sciences, vol. 104, No. 5, pp. 1482-1487 (Jan. 30, 2007).
Langer, R., "Drug delivery and targeting", Nature, vol. 392, No. 6679, pp. 5-10 (Apr. 30, 1998).
Lavasanifar et al., "Poly(ethylene oxide)-block-poly(L-amino acid) micelles for drug delivery", Advanced Drug Delivery Reviews, vol. 54, pp. 169-190 (2002).
Li et al., "Pharmacokinetics and Biodistribution of Nanoparticles", Molecular Pharmaceutics, vol. 5, No. 4, pp. 496-504 (2008).
Liang et al., "Preparation of nanoparticles composed of poly(gamma-glutamic acid)-poly(lactide) block copolymers and evaluation of their uptake by HepG2 cells", J. Controlled Release, vol. 105, pp. 213-225 (2005).
Liu et al., "CFD Predictions for Chemical Processing in a Confined Impinging-Jets Reactor", AIChE Journal, vol. 52, No. 2, pp. 731-744 (Feb. 2006).
Liu et al., "Janus Colloids Formed by Biphasic Grafting at a Pickering Emulsion Interface", Angew. Chem., vol. 120, pp. 4037-4039 (2008).
Liu, Y. et al., "Mixing in a multi-inlet vortex mixer (MIVM) for flash nano-precipitation", Chemical Engineering Science, (2008), vol. 63, No. 11, pp. 2829-2842.
Liu et al., "Ostwald Ripening of beta-Carotene Nanoparticles", Phys. Rev. Lett., vol. 98, No. 3, pp. 036102-1-036102-4 (2007).
Livraghi et al., "Cystic Fibrosis and Other Respiratory Diseases of Impaired Mucus Clearance", Toxicologic Pathology, vol. 35, No. 1, pp. 116-129 (2007).
Lu et al., "Hydrophobic Ion Pairing of Peptide Antibiotics for Processing into Controlled Release Nanocarrier Formulations", Molecular Pharmaceutics, vol. 15, No. 1, pp. 216-225 (2018).
Luo et al., "Synthetic DNA delivery systems", Nature Biotechnology, vol. 18, No. 1, pp. 33-37 (Jan. 2000).
Mai et al., "Controlled Incorporation of Particles into the Central Portion of Vesicle Walls", J. Am. Chem. Soc., vol. 132, pp. 10078-10084 (2010).
Marcus et al., "Ion Pairing", Chemical Reviews, vol. 106, No. 11, pp. 4585-4621 (2006).
Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).
Matschiner et al., "Optimization of Topical Erythromycin Formulations by Ion Pairing", Skin Pharmacology: The Official Journal of the Skin Pharmacology Society, vol. 8, No. 6, pp. 319-325 (1995).
Meyer et al., "Hydrophobic Ion Pairing: Altering the Solubility Properties of Biomolecules", Pharmaceutical Research, vol. 15, No. 2, pp. 188-193 (1998).
Mitragotri et al., "Overcoming the challenges in administering biopharmaceuticals: formulation and delivery strategies", Nat. Rev. Drug Discov., vol. 13, No. 9, pp. 655-672 (41 pages) (Sep. 2014).
Muehle et al., "Stability of Particle Aggregates in Flocculation with Polymers: Stabilitaet von Teilchenaggregaten bei der Flockung mit Polymeren", Chemical Engineering & Processing: Process Intensification, vol. 29, No. 1, pp. 1-8 (1991).
Mueller et al., "Solid lipid nanoparticles (SLN) for controlled drug delivery—a review of the state of the art", European Journal of Pharmaceutics & Biopharmaceutics, vol. 50, No. 1, pp. 161-177 (2000).
Muheem et al., "A review on the strategies for oral delivery of proteins and peptides and their clinical perspectives", Saudi Pharmaceutical Journal, vol. 24, No. 4, pp. 413-428 (2016).
O'Reilly et al., "Cross-linked block copolymer micelles: functional nanostructures of great potential and versatility", Chemical Society Reviews, vol. 35, pp. 1068-1083 (2006).

Okuyama et al., "Preparation of functional nanostructured particles by spray drying", Advanced Powder Technol., vol. 17, No. 6, pp. 587-611 (2006).
Overbeek et al., "Phase separation in polyelectrolyte solutions. Theory of complex coacervation", Journal of Cellular Physiology, vol. 49, No. S1, pp. 7-26 (1957).
Owens et al., "Opsonization, biodistribution, and pharmacokinetics of polymeric nanoparticles", International Journal of Pharmaceutics, vol. 307, No. 1, pp. 93-102 (2006).
Pagels et al., "Inverse Flash NanoPrecipitation for Biologics Encapsulation: Nanoparticle Formation and Ionic Stabilization in Organic Solvents", ACS Publications, vol. 1271, pp. 249-274 (2017).
Pagels et al., "Polymeric nanoparticles and microparticles for the delivery of peptides, biologics, and soluble therapeutics", Journal of Controlled Release, vol. 219, pp. 519-535 & Supplemental Information (2015).
Patil et al., "Retention of trypsin activity in spermine alginate microcapsules", Journal of Microencapsulation, vol. 14, No. 4, pp. 469-474 (1997).
Pattni et al., "New Developments in Liposomal Drug Delivery", Chemical Reviews, vol. 115, No. 19, pp. 10938-10966 (2015).
Peters et al., "Biotech Products in Big Pharma Clinical Pipelines Have Grown Dramatically According to the Tufts Center for the Study of Drug Development", Nov. 14, 2013, https://www.biospace.com/... a-clinical-pipelines-have-grown-dramatically-according-to-the-tufts-center-for-the-study-of-drug-development-/, accessed Aug. 29, 2018 (5 pages).
Pham et al., "Micellar Solutions of Associative Triblock Copolymers: Entropic Attraction and Gas-Liquid Transition", Macromolecules, vol. 32, No. 9, pp. 2996-3005 (1999).
Pinkerton et al., "Formation of Stable Nanocarriers by in Situ Ion Pairing during Block-Copolymer-Directed Rapid Precipitation", Molecular Pharmaceutics, vol. 10, No. 1, pp. 319-328 (2013).
Pitt, "The controlled parenteral delivery of polypeptides and proteins", International Journal of Pharmaceutics, vol. 59, pp. 173-196 (1990).
Pustulka et al., "Flash Nanoprecipitation: Particle Structure and Stability", Molecular Pharmaceutics, vol. 10, pp. 4367-4377 (2013).
Qi et al., "Determination of the Bioavailability of Biotin Conjugated onto Shell Cross-Linked (SCK) Nanoparticles", Journal American Chemical Society, vol. 126, pp. 6599-6607 (2004).
Reinhold et al., "Self-healing Microencapsulation of Biomacromolecules without Organic Solvents", Angew. Chem. Int. Ed. Engl., vol. 51, No. 43, pp. 10800-10803 (9 pages) (Oct. 22, 2012).
Reinhold et al., "Self-Healing Microencapsulalion of Biomacromolecules without Organic Solvents", Angewandte Chemie, vol. 124, Issue 43, pp. 10958-10961 (6 pages) (Oct. 2012).
Riess et al. "Emulsifying Properties of Block Copolymers. Oil-Water Emulsions and Microemulsions", Polym. Eng. Sci., vol. 17, No. 8, pp. 634-638 (1977).
Radler et al., "Structure of DNA-Cationic Liposome Complexes: DNA Intercalation in Multilamellar Membranes in Distinct Interhelical Packing Regimes", Science, vol. 275, No. 5301, pp. 810-814 (Feb. 7, 1997), DOI: 10.1126/science.275.5301.810.
Saad, W.S. & Prud'Homme, R.K., "Principles of nanoparticle formation by flash nanoprecipitation", Nano Today, vol. 11, No. 2, pp. 212-227 (2016).
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).
Salentinig et al., "Self-Assembled Structures and pKa Value of Oleic Acid in Systems of Biological Relevance", Langmuir, vol. 26, No. 14, pp. 11670-11679 (2010). DOI: 10.1021/la101012a.
Sato et al., "Therapeutic peptides: technological advances driving peptides into development", Current Opinion in Biotechnology, vol. 17, pp. 638-642 (2006).
Savjani, K.T. et al., "Drug Solubility: Importance and Enhancement Techniques", ISRN Pharmaceutics, vol. 2012, Article ID 195727, pp. 1-10 (2012).
Schwendeman et al., "Injectable controlled release depots for large molecules", Journal of Controlled Release, vol. 190, pp. 240-253 (37 pages) (Sep. 28, 2014).

(56) References Cited

OTHER PUBLICATIONS

Serajuddin, "Salt formation to improve drug solubility", Advanced Drug Delivery Reviews, vol. 59, No. 7, pp. 603-616 (2007).
Shah et al., Poly(glycolic acid-co-DL-lactic acid): diffusion or degradation controlled drug delivery?, Journal of Controlled Release, vol. 18, pp. 261-270 (1992).
Sheela, D.L. et al., "Lauric acid induce cell death in colon cancer cells mediated by the epidermal growth factor receptor downregulation: An in silico and in vitro study", Human & Experimental Toxicology, (Epub. Apr. 3, 2019) pp. 1-9, DOI: 10.1177/0960327119839185.
Sohn et al., "Polymer prodrug approaches applied to paclilaxel", Polymer Chemistry, vol. 1, No. 6, pp. 778-792 (2010).
Solaro et al., "Targeted Delivery of Protein Drugs by Nanocarriers", Materials, vol. 3, No. 3, pp. 1928-1980 (2010).
Song et al., "A novel in situ hydrophobic ion pairing (HIP) formulation strategy for clinical product selection of a nanoparticle drug delivery system", Journal of Controlled Release, vol. 229, pp. 106-119 (2016).
Sosa et al., "Soft Multifaced and Patchy Colloids by Constrained Volume Self-Assembly", Macromolecules, vol. 49, pp. 3580-3585 (2016).
Steichen et al., "A review of current nanoparticle and targeting moieties for the delivery of cancer therapeutics", European J. Pharmaceutical Sciences, vol. 48, pp. 416-427 (2013).
Talelli et al., "Core-crosslinked polymeric micelles: Principles, preparation, biomedical applications and clinical translation", Nano Today, vol. 10, pp. 93-117 (2015).
Turro et al., "Spectroscopic Probe Analysis of Protein-Surfactant Interactions: The BSA/SDS System", Langmuir, vol. 11, No. 7, pp. 2525-2533 (1995).
U.S. Appl. No. 15/321,588 Notice of Allowance & Notice of Allowability dated Oct. 24, 2018.
U.S. Appl. No. 15/321,588 Office Action dated Apr. 10, 2018.
U.S. Appl. No. 15/321,588 Restriction/Election Requirement dated Dec. 1, 2017.
U.S. Appl. No. 15/321,588, filed Oct. 24, 2018 dated Summary of Examiner Interview of Oct. 9, 2018.
U.S. Appl. No. 16/064,935 Notice of Allowability dated Aug. 2, 2021.
U.S. Appl. No. 16/064,935 Notice of Allowability dated Jun. 21, 2021.
U.S. Appl. No. 16/064,935 Notice of Allowance & Notice of Allowability dated Oct. 21, 2020.
U.S. Appl. No. 16/064,935 Notice of Allowance & Notice of Allowability dated Apr. 28, 2021.
U.S. Appl. No. 16/064,935 Notice of Allowance & Notice of Allowability dated May 6, 2020.
U.S. Appl. No. 16/064,935 Restriction/Election Requirement dated Jan. 13, 2020.
U.S. Appl. No. 16/253,850 Restriction/Election Requirement dated Apr. 7, 2020.
U.S. Appl. No. 16/253,850 Office Action dated Sep. 8, 2020.
Aggarwal et al., "What's fueling the biotech engine—2012 to 2013", Nat. Biotechnol., vol. 32, No. 1, pp. 32-39, Jan. 2014.
Ansell et al., "Modulating the Therapeutic Activity of Nanoparticle Delivered Paclitaxel by Manipulating the Hydrophobicity of Prodrug Conjugates", Journal of Medicinal Chemistry, vol. 51, No. 11, pp. 3288-3296 (2008).
Anton et al., "Aqueous-Core Lipid Nanocapsules for Encapsulating Fragile Hydrophilic and/or Lipophilic Molecules", Langmuir, vol. 25, No. 19, pp. 11413-11419 (2009).
Antonietti et al., "Polyelectrolyte-Surfactant Complexes: A New Type of Solid, Mesomorphous Material", Macromolecules, vol. 27, No. 21, pp. 6007-6011 (1994).
Antonov et al., "Entering and Exiting the Protein—Polyelectrolyte Coacervate Phase via Nonmonotonic Salt Dependence of Critical Conditions", Biomacromolecules, vol. 11, No. 1, pp. 51-59 (2010).

Arshady, "Preparation of biodegradable microspheres and microcapsules: 2. Polyactides and related polyesters", Journal of Controlled Release, vol. 17, pp. 1-22 (1991).
Babu, N.J. & Nangia, A., "Solubility Advantage of Amorphous Drugs and Pharmaceutical Cocrystals", Crystal Growth & Design, vol. 11, pp. 2662-2679 (2011).
Bailly, N. et al. "Poly(N-vinylpyrrolidone)-block-poly(vinyl acetate) as a Drug Delivery Vehicle for Hydrophobic Drugs", Biomacromolecules, vol. 13, pp. 4109-4117 (2012).
BASF, Luviscol VA Grades Technical Information, Jun. 2012, pp. 1-14.
Bilati et al., "Development of a nanoprecipitation method intended for the entrapment of hydrophilic drugs into nanoparticles", European J. Pharmaceutical Sciences, vol. 24, pp. 67-75 (2005).
Bontha et al., "Polymer micelles with cross-linked ionic cores for delivery of anticancer drugs", Journal of Controlled Release, vol. 114, pp. 163-174 (2006).
Bronich et al., "Polymer Micelle with Cross-Linked Ionic Core", J. Am. Chem Soc., vol. 127, pp. 8236-8237 (2005).
Bronich et al., "Soluble Complexes from Poly(ethylene oxide)-block-polymethacrylate Anions and N-Alkylpyridinium Cations", Macromolecules, vol. 30, pp. 3519-3525 (1997).
Bruno et al., Basics and recent advances in peptide and protein drug delivery, Therapeutic Delivery, vol. 4, No. 11, pp. 1443-1467 (45 pages) (2013).
Colombani et al., "Structure of Micelles of Poly(n-butyl acrylate)-block-poly(acrylic acid) Diblock Copolymers in Aqueous Solution", Macromolecules, vol. 40, pp. 4351-4362 (2007).
Colombani et al., "Synthesis of Poly(n-butyl acrylate)-block-poly(acrylic acid) Diblock Copolymers by ATRP and Their Micellization in Water", Macromolecules, vol. 40, pp. 4338-4350 (2007).
"The Complete Guide to Enteric Coating", https://astenzymes.com/the-complete-guide-to-enteric-coating/, pp. 1-11, accessed Aug. 11, 2020.
Crater et al., "Barrier Properties of Gastrointestinal Mucus to Nanoparticle Transport," Macromolecular Bioscience, vol. 10, No. 12, pp. 1473-1483 (2010).
Cu et al., "Drug delivery: Stealth particles give mucus the slip", Nature Materials, vol. 8, No. 1, pp. 11-13 (Jan. 2009).
D'Addio & Prud'Homme, "Controlling drug nanoparticle formation by rapid precipitation", Advanced Drug Delivery Reviews, vol. 63, No. 6, pp. 417-426 (2011).
Davies et al., "Recent advances in the management of cystic fibrosis", Archives of Disease in Childhood, vol. 99, No. 11, pp. 1033-1036 (2014).
Deng et al., "Janus Nanoparticles of Block Copolymers by Emulsion Solvent Evaporation Induced Assembly", Macromolecules, vol. 49, pp. 1362-1368 (2016).
Eghbali et al., "Rheology and Phase Behavior of Poly(n-butyl acrylate)-block-poly(acrylic acid) in Aqueous Solution", Langmuir, vol. 22, pp. 4766-4776 (2006).
Ensign et al., "Oral drug delivery with polymeric nanoparticles: The gastrointestinal mucus barriers", Advanced Drug Delivery Reviews, vol. 64, No. 6, pp. 557-570 (2012).
Erre et al., "Chromium(III) Acetate, Chromium(III) Acetate Hydroxide, or mu3-Oxo-esakis-(mu2-acetato-O,O')- triaqua-trichromium(III) Acetate?", Journal of Chemical Education, vol. 74, No. 4, pp. 432-435 (Apr. 1997).
Extended European Search Report (EESR) dated Jan. 8, 2018 in European Application No. 15811879.4.
"Enteric Coating—The Enteric Coating Process", https://www.xtend-life.com/pages/enteric-coating, pp. 1-6, accessed Aug. 12, 2020.
Etchenausia, L. et al., "RAFT/MADIX emulsion copolymerization of vinyl acetate and N-vinylcaprolactam: towards waterborne physically crosslinked thermoresponsive particles", Polymer Chemistry, DOI: 10.1039/C7PY00221A, pp. 1-28 (2017).
Foerster et al., "Amphiphilic Block Copolymers in Structure-Controlled Nanomaterial Hybrids", Advanced Materials, vol. 10, No. 3, pp. 195-217 (1998).
Galindo-Rodriguez et al., "Polymeric Nanoparticles for Oral Delivery of Drugs and Vaccines: A Critical Evaluation of In Vivo Studies", Critical Reviews in Therapeutic Drug Carrier Systems, vol. 22, No. 5, pp. 419-463 (2005).

(56) References Cited

OTHER PUBLICATIONS

Gao et al., "Core Cross-Linked Reverse Micelles from Star-Shaped Polymers", Chemistry of Materials, vol. 20, pp. 3063-3067 (2008).
Gaudana et al., "Design and evaluation of a novel nanoparticulate-based formulation encapsulating a HIP complex of lysozyme", Pharmaceutical Development & Technology, vol. 18, No. 3, pp. 752-759 (2013).
Gindy et al., "Mechanism of Macromolecular Structure Evolution in Self-Assembled Lipid Nanoparticles for siRNA Delivery", Langmuir, vol. 30, No. 16, pp. 4613-4622 (2014).
Google Scholar NPL search string—downloaded Apr. 29, 2020, 1 page.
Gregory et al., "Adsorption and flocculation by polymers and polymer mixtures", Advances in Colloid & Interface Science, vol. 169, No. 1, pp. 1-12 (2011).
Groeschel et al., "Guided hierarchical co-assembly of soft patchy nanoparticles", Nature, vol. 503, pp. 247-251 (5 pages & 11 pages Methods, Extended Data Figures 1-9, & Extended Data Table 1) (Nov. 14, 2013).
Guo, Q. et al., "Binding of dihydromyricetin and its metal ion complexes with bovine serum albumin", Biotechnology & Biotechnological Equipment, vol. 28, No. 2, pp. 333-341 (2014).
Guo, Q. et al., "Biosynthesis of gold nanoparticles using a kind of flavanol: Dihydromyricetin", Colloids & Surfaces A: Physicochem. & Engineering Aspects, vol. 441, pp. 127-132 (2014).
Guo, Q. et al., "Synthesis of dihydromyricetin-manganese (II) complex and interaction with DNA", J. Molecular Structure, vol. 1027, pp. 64-69 (2012).
Holland et al., "Polymers for Biodegradable Medical Devices, 1. The Potential of Polyesters As Controlled by Macromolecular Release Systems", Journal of Controlled Release, vol. 4, pp. 155-180 (1986).
Horigome et al., "Long-Time Relaxation of Suspensions Flocculated by Associating Polymers", Langmuir, vol. 18, No. 5, pp. 1968-1973 (2002).
Høiby, "Recent advances in the treatment of Pseudomonas aeruginosa infections in cystic fibrosis", BMC Medicine, vol. 9, No. 32, pp. 1-7 (2011).
Ilton et al., "Direct Measurement of the Critical Pore Size in a Model Membrane", Physical Review Letters, 117, Issue 25, pp. 257801-1 through 257801-5 (Dec. 16, 2016).
Immordino et al., "Stealth liposomes: review of the basic science, rationale, and clinical applications, existing and potential", International Journal of Nanomedicine, vol. 1, No. 3, pp. 297-315 (2006).
International Patent Application PCT/US2015/017590 International Search Report and Written Opinion dated Jul. 16, 2015.
International Patent Application PCT/US2015/036060 International Search Report and Written Opinion dated Sep. 18, 2015.
International Patent Application PCT/US2016/068145 International Search Report and Written Opinion dated Mar. 23, 2017.
International Patent Application PCT/US2017/054779 International Search Report and Written Opinion dated Jan. 26, 2018.
International Patent Application PCT/US2018/050714 International Preliminary Report on Patentability mailed Mar. 26, 2020 (Issued Mar. 17, 2020).
International Patent Application PCT/US2018/049580 International Search Report and Written Opinion dated Jan. 15, 2019.
Kader & Jalil, "In Vitro Release of Theophylline from Poly(Lactic Acid) Sustained-Release Pellets Prepared by Direct Compression", Drug Development & Industrial Pharmacy, vol. 24, Issue 6, pp. 527-534 (1998).
Lan et al., "Preparation and Characterization of Super Cross-Linked Poly(ethylene oxide) Gel Polymer Electrolyte for Lithium-Ion Battery", Science of Advanced Materials, vol. 9, No. 6, pp. 988-994 (2017).
U.S. Appl. No. 17/260,640 Office Action dated Oct. 30, 2023.
U.S. Appl. No. 17/260,640 Notice of Allowance & Notice of Allowability dated Mar. 13, 2024.
U.S. Appl. No. 17/260,640, filed Mar. 13, 2024 dated Summary of Interview of Feb. 29, 2024.
U.S. Appl. No. 16/253,850 U.S. Patent & Trademark Office (USPTO) Communication dated Mar. 9, 2021.
U.S. Appl. No. 16/253,850 Notice of Allowance & Notice of Allowability dated Apr. 12, 2022.
U.S. Appl. No. 16/253,850, filed Aug. 11, 2021 dated Summary of Interview of Aug. 9, 2021.
U.S. Appl. No. 16/253,850 Office Action dated Sep. 23, 2021.
U.S. Appl. No. 16/253,850 Notice of Allowance & Notice of Allowability dated Sep. 13, 2022.
U.S. Appl. No. 16/253,850 Supplemental Notice of Allowability dated Dec. 19, 2022.
U.S. Appl. No. 16/517,510 Restriction/Election Requirement dated Mar. 19, 2021.
U.S. Appl. No. 16/517,510 Office Action dated Sep. 24, 2021.
U.S. Appl. No. 16/517,510 Notice of Allowance & Notice of Allowability dated May 9, 2022.
U.S. Appl. No. 16/517,510 Notice of Allowance & Notice of Allowability dated Nov. 23, 2022.
U.S. Appl. No. 16/517,510 Notice of Allowance & Notice of Allowability dated Apr. 19, 2023.
U.S. Appl. No. 16/816,241 Office Action dated May 12, 2022.
U.S. Appl. No. 16/816,241 Restriction/Election Requirement dated Sep. 30, 2021.
U.S. Appl. No. 16/816,241 Notice of Allowance & Notice of Allowability dated Nov. 16, 2022.
U.S. Appl. No. 16/816,241 Notice of Allowance & Notice of Allowability dated Mar. 7, 2023.
U.S. Appl. No. 16/816,241 Notice of Allowance & Notice of Allowability dated Apr. 13, 2023.
U.S. Appl. No. 16/810,710 Restriction/Election Requirement dated Jan. 6, 2021.
U.S. Appl. No. 16/810,710 Office Action dated May 12, 2021.
U.S. Appl. No. 16/810,710 Office Action dated Mar. 30, 2022.
U.S. Appl. No. 17/899,157 Restriction/Election Requirement dated Oct. 30, 2023.
U.S. Appl. No. 17/899,157 Office Action dated Apr. 10, 2024.
Vyavahare et al., "Analysis of Structural Rearrangements of Poly(lactic acid) in the Presence of Water", Journal Physical Chemistry B, vol. 118, No. 15, pp. 4185-4193 (2014).
Wang et al., "Characterization of the initial burst release of a model peptide from poly(D,L-lactide-co-glycolide) rnicrospheres", J. Controlled Release, vol. 82, pp. 289-307 (2002).
Xu et al., "Scalable method to produce biodegradable nanoparticles that rapidly penetrate human mucus", Journal of Controlled Release, vol. 170, pp. 279-286 (2013).
Yu et al., "Nanotechnology for Protein Delivery: Overview and Perspectives", J. Controlled Release, vol. 240, pp. 24-37 (32 pages) (Oct. 28, 2016).
Zandonella, "Bob Prud'homme—Flash NanoPrecipitation" http://research.princeton.edu/news/features/a/index.xml?id=6234, accessed Mar. 9, 2018, originally published Dec. 9, 2011, pp. 1-2.
Zhang et al., "Development of Nanoparticles for Antimicrobial Drug Delivery", Current Medicinal Chemistry, vol. 17, No. 5, pp. 585-594 (2010).
Zhang et al., "Amphiphilic cylindrical brushes with poly(acrylic acid) core and poly(n-butyl acrylate) shell and narrow length distribution", Polymer, vol. 44, No. 5, pp. 1449-1458 (2003).
Zhu et al., "Preparation and characterization of hCG-loaded polylactide or poly(lactide-co-glycolide) microspheres using a modified water-in-oil-in-water (w/o/w) emulsion solvent evaporation technique", J. Microencapsulation, vol. 18, No. 2, pp. 247-260 (2001).
Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).
Hadinoto et al., "Lipid-polymer hybrid nanoparticles as a new generation therapeutic delivery platform: A review", European Journal of Pharmaceutics & Biopharmaceutics, vol. 85, No. 3, part A, pp. 427-443 (2013).

(56) References Cited

OTHER PUBLICATIONS

Kauffman et al., "Materials for non-viral intracellular delivery of messenger RNA therapeutics", J. Controlled Release, vol. 240, pp. 227-234 (2016).

* cited by examiner polymyxin B sulfate colistin ("polymyxin E")

HYDROPHOBIC ION PAIRING AND FLASH NANOPRECIPITATION FOR FORMATION OF CONTROLLED-RELEASE NANOCARRIER FORMULATIONS

This application is a U.S. National Stage (Section 371) of International Application No. PCT/US2018/058869, filed Nov. 2, 2018, which was published in the English language on May 9, 2019 as International Publication No. WO/2019/090030, which claims the benefit of U.S. Provisional Application No. 62/581,394, filed Nov. 3, 2017, all of which are incorporated by reference in their entireties herein.

This invention was made with government support under Grant No. GM-066134 awarded by the National Institutes of Health and Grant No. CNS-0612345 awarded by the National Science Foundation. The government has certain rights in the invention.

Incorporated by reference is the file 8857-0049_ST25_SequenceListing.txt, which was created on Jul. 12, 2024 and has a size of 889 bytes.

BACKGROUND OF THE INVENTION

Sequestration of active pharmaceutical ingredients (APIs) into drug carriers has been considered for producing formulations with biological efficacy.

SUMMARY OF THE INVENTION

In an embodiment of the invention, a nanoparticle includes a modified salt including a water-soluble active pharmaceutical ingredient (API) ion paired with a hydrophobic counterion of an ion pairing (IP) reagent and a nanoparticle encapsulant material substantially surrounding the modified salt. The API can be an antibacterial and/or a biologic. The API can be an antimicrobial small molecule, a peptide, a protein, or an aminoglycoside. The API can have an aqueous solubility of greater than 10 mg/ml, a logP value less than -2 in an aqueous solution at pH of 7, and/or 1, 2, 3, 4, 5, 6, or more ionic groups. The API can be other than an oligonucleotide. The API can be gentamycin, polymyxin B, mastoparan 7, sub5, LL37, colistin, ecumicin, OZ439, ovalbumin, or lysozyme.

The counterion can have a logP value of 2 or greater at a pH of 7. The counterion can have a logP value of greater than 5, and the release profile of the API can exhibit a plateau in the release rate with time. The counterion can have 1, 2, or more ionic sites. The counterion can be an anionic counterion that has a pKa value of from −2 to 5. The counterion can have a pKb value of greater than 3. The counterion can be a quaternized cationic species. The counterion can have an ionic site selected from the group consisting of a carboxylic acid, sulfate, sulfonate, or amine. The IP reagent can be sodium hexanoate, sodium decanoate, benzenesulfonic acid monohydrate, sodium 2-naphthalenesulfonate, (1R)-(−)-10-camphorsulfonic acid, sodium 1,2-ethanesulfonate, sodium 1-heptanesulfonate, sodium 1-octanesulfonate monohydrate, sodium 1-decanesulfonate, or sodium deoxycholate. The IP reagent can be sodium dodecyl sulfate (SDS), sodium decyl sulfate (DS), sodium dodecylbenzene sulfonate (DBS), sodium myristate (MA), sodium oleate (OA), or pamoic acid disodium salt (PA). The counterion can be dodecyl hydrogen sulfate, decyl hydrogen sulfate, dodecylbenzene sulfonic acid, or myristic acid. The counterion can be oleic acid or pamoic acid.

The nanoparticle encapsulant material can be a self-assembling material. The nanoparticle encapsulant material can be hydroxypropyl methylcellulose acetate succinate (HPMCAS), polystyrene-block-polyethylene glycol (PS-b-PEG), or polycaprolactone-block-polyethylene glycol (PCL-b-PEG). For example, the nanoparticle encapsulant material can be 1.6 kDa polystyrene-block-5 kDa polyethylene glycol or 5 kDa polycaprolactone-block-5 kDa polyethylene glycol.

The nanoparticle can include a polyethylene glycol coating on the nanoparticle.

The nanoparticle can have a particle size of from 10 nm to 1000 nm, from 10 nm to 1200 nm, from 25 nm to 1000 nm, from 50 nm to 500 nm, from 75 nm to 400 nm, from 100 nm to 350 nm, from 100 nm to 250 nm, or from 100 nm to 150 nm.

The API and a supplemental hydrophobic compound can be co-encapsulated within the nanoparticle. For example, the supplemental hydrophobic compound can be a therapeutic, imaging agent, or agrochemical compound.

The API can include gentamycin, polymyxin B, mastoporan 7, sub5, LL37, colistin, ecumicin, OZ439, ovalbumin, or lysozyme. The API can include an antimicrobial small molecule, for example, an antimicrobial small molecule having a molecular weight of less than 1000 Da. The API can include an aminoglycoside, for example, a 4,6-disubstituted deoxystreptamine trisaccharide. The API can include an oligopeptide, such as a linear oligopeptide or a cyclic oligopeptide, which can have a molecular weight of from 1000 Da to 2000 Da. The API can include a protein, such as an anionic protein or a cationic protein, which can have a molecular weight of greater than 2000 Da.

The IP reagent can include sodium dodecyl sulfate (SDS), sodium decyl sulfate (DS), sodium dodecylbenzene sulfonate (DBS), sodium myristate (MA), sodium oleate (OA), pamoic acid disodium salt (PA), vitamin E succinate, or sodium dextran sulfate (DXS). The counterion can include dodecyl hydrogen sulfate, decyl hydrogen sulfate, dodecylbenzene sulfonic acid, myristic acid, oleic acid, pamoic acid, vitamin E succinic acid, or dextran hydrogen sulfate, or a salt, such as an alkali metal (e.g., lithium (Li), sodium (Na), potassium (K), rubidium (Rb), or caesium (Cs)) salt, of any of these. The counterion can include a fatty acid, an alkyl hydrogen sulfate, an alkylsulfonic acid, an alkyl quaternary ammonium cation, or a salt, such as an alkali metal salt, of any of these.

The nanoparticle encapsulant material can include hydroxypropyl methylcellulose acetate succinate (HPMCAS), polystyrene-block-polyethylene glycol (PS-b-PEG), or polycaprolactone-block-polyethylene glycol (PCL-b-PEG). The nanoparticle encapsulant material can include a block copolymer, such as an amphiphilic block copolymer, which can have a molecular weight of about 10 kDa or less.

In an embodiment the active pharmaceutical ingredient is gentamycin, the ion pairing reagent is sodium dodecyl sulfate (SDS), and the nanoparticle encapsulation material is polycaprolactone-block-polyethylene glycol block copolymer. In an embodiment the active pharmaceutical ingredient is polymyxin B, the ion pairing reagent is sodium dodecyl sulfate (SDS), and the nanoparticle encapsulation material is polycaprolactone-block-polyethylene glycol block copolymer. In an embodiment, the active pharmaceutical ingredient is polymyxin B, the ion pairing reagent is sodium dodecylbenzene sulfonate (DBS), and the nanoparticle encapsulation material is polycaprolactone-block-polyethylene glycol block copolymer. In an embodiment the active pharmaceutical ingredient is polymyxin B, the ion pairing reagent is sodium oleate, and the nanoparticle encapsulation material is polycaprolactone-block-polyethylene glycol block copolymer. In an embodiment, the active pharmaceutical ingredient is mastoporan 7, the ion pairing reagent is sodium dodecyl sulfate (SDS), and the nanoparticle encapsulation material is polycaprolactone-block-polyethylene glycol block copolymer. In an embodiment the active pharmaceutical ingredient is sub5, the ion pairing reagent is sodium dodecyl sulfate (SDS), and the nanoparticle encapsulation material is polycaprolactone-block-polyethylene glycol block copolymer. In an embodiment, the active pharmaceutical ingredient is LL37, the ion pairing reagent is sodium dodecyl sulfate (SDS), and the nanoparticle encapsulation material is polycaprolactone-block-polyethylene glycol block copolymer. In an embodiment, the active pharmaceutical ingredient is colistin, the ion pairing reagent is sodium oleate, and the nanoparticle encapsulation material is polycaprolactone-block-polyethylene glycol block copolymer. In an embodiment, the active pharmaceutical ingredient is ecumicin, the ion pairing reagent is vitamin E succinate, and the nanoparticle encapsulation material is polycaprolactone-block-polyethylene glycol block copolymer. In an embodiment, the active pharmaceutical ingredient is OZ439, the ion pairing reagent is sodium oleate, and the nanoparticle encapsulation material is hydroxypropyl methylcellulose acetate succinate (HPMCAS). In an embodiment, the active pharmaceutical ingredient is ovalbumin, the ion pairing reagent is a quaternary ammonium surfactant, and the nanoparticle encapsulation material is polycaprolactone-block-polyethylene glycol block copolymer. In an embodiment, the active pharmaceutical ingredient is ovalbumin, the ion pairing reagent is cetyl trimethylammonium bromide, and the nanoparticle encapsulation material is polycaprolactone-block-polyethylene glycol block copolymer. In an embodiment, the active pharmaceutical ingredient is lysozyme, the ion pairing reagent is sodium oleate, and the nanoparticle encapsulation material is polycaprolactone-block-polyethylene glycol block copolymer. In an embodiment, the active pharmaceutical ingredient is lysozyme, the ion pairing reagent is sodium dodecyl sulfate (SDS), and the nanoparticle encapsulation material is polycaprolactone-block-polyethylene glycol block copolymer. In an embodiment, the active pharmaceutical ingredient is lysozyme, the ion pairing reagent is dextran sulfate (DXS) polymer, and the nanoparticle encapsulation material is polycaprolactone-block-polyethylene glycol block copolymer.

A method of the invention for encapsulating an active pharmaceutical ingredient (API) includes producing a hydrophobic salt by ion pairing charged functional groups on a water soluble API with an ion pairing (IP) reagent and forming nanoparticles that are carriers of the hydrophobic salt to encapsulate the API, with the IP reagent including a counterion for the API. Producing a hydrophobic salt can include mixing the API and the IP in water to form a water-insoluble precipitate as the hydrophobic salt, removing the water, and dissolving the water-insoluble precipitate into an organic solvent. A polymer can be dissolved into the organic solvent. The organic solvent can be water-miscible.

The dissolved water-insoluble precipitate can be used in an organic stream to form the nanoparticles by flash nanoprecipitation.

The solution of the hydrophobic salt dissolved in the organic solvent can be continuously mixed with a polar solvent to form a mixed solution from which the nanoparticles assemble and precipitate.

Producing a hydrophobic salt can include dissolving the API in a water stream, dissolving the IP in an organic stream, and forming a water-insoluble precipitate as the hydrophobic salt through micro-mixing the organic stream against the water stream in a Flash NanoPrecipitation (FNP) process. A polymer can be dissolved into the organic stream. The organic stream can be water-miscible.

The nanoparticles can be formed by dissolving the API in a polar solvent to form a polar solution stream, dissolving the IP in an organic solvent to form an organic solution stream, and continuously mixing the polar solution stream against the organic solution stream to form a mixed solution from which the nanoparticles that encapsulate the API assemble and precipitate, and the organic solvent can be less polar than the polar solvent. A polymer can be dissolved into the organic solvent. The organic solvent can be water-miscible.

The nanoparticles can be formed by an emulsion/stripping process.

The API can be an antibacterial and/or a biologic. The API can be an antimicrobial small molecule, a peptide, a cationic peptide, an anionic peptide, a protein, a cationic protein, an anionic protein, or an aminoglycoside. The API can have an aqueous solubility of greater than 10 mg/ml, can have a logP value less than-2 in an aqueous solution at pH of 7, and/or can have 1, 2, 3, 4, 5, 6, or more ionic groups. The API can be other than an oligonucleotide. The API can be gentamycin, polymyxin B, mastoparan 7, sub5, LL37, colistin, ecumicin, OZA39, ovalbumin, or lysozyme. The API can be gentamycin, polymyxin B, mastoparan 7, sub5, colistin, or ovalbumin.

The counterion can have a logP value of 2 or greater at a pH of 7. The counterion can have a logP value of greater than 5. The release profile of the API can exhibit a plateau in the release rate (or fraction released) with time. The counterion can have 1, 2, or more ionic sites. The counterion can be an anionic counterion that has a pKa value of from −2 to 5. The counterion can have a pKb value of greater than 3. The counterion can be a quaternized cationic species, for example, a quaternized cationic species that is permanently cationic. The counterion can have an ionic site selected from the group consisting of a carboxylic acid, sulfate, sulfonate, or amine. The IP reagent can be sodium hexanoate, sodium decanoate, sodium myristate (MA), sodium oleate (OA), pamoic acid disodium salt (PA), benzenesulfonic acid monohydrate, sodium 2-naphthalenesulfonate, (1R)-(−)-10-camphorsulfonic acid, sodium 1,2-ethanesulfonate, sodium 1-heptanesulfonate, sodium 1-octanesulfonate monohydrate, sodium 1-decanesulfonate, sodium dodecyl sulfate (SDS), sodium dodecylbenzene sulfonate (DBS), sodium deoxycholate, or sodium decyl sulfate (DS). The counterion can be dodecyl hydrogen sulfate, decyl hydrogen sulfate, dodecylbenzene sulfonic acid, or myristic acid. The counterion can be oleic acid or pamoic acid.

The polymer can be self-assembling. The polymer can be hydroxypropyl methylcellulose acetate succinate (HPMCAS), polystyrene-block-polyethylene glycol (PS-b-PEG), or polycaprolactone-block-polyethylene glycol (PCL-b-PEG). For example, the polymer can be 1.6 kDa polystyrene-block-5 kDa polyethylene glycol or 5 kDa polycaprolactone-block-5 kDa polyethylene glycol.

The nanoparticles can include a polyethylene glycol coating.

The nanoparticles can have a Z-average particle size of from 10 nm to 1000 nm, from 25 nm to 1200 nm, from 50 nm to 500 nm, from 75 nm to 400 nm, from 100 nm to 350 nm, from 100 nm to 250 nm, or from 100 nm to 150 nm. The nanoparticles can have a polydispersity index (PDI) of from 0.06 to 0.5, from 0.07 to 0.34, from 0.08 to 0.27, from 0.1 to 0.2, or from 0.12 to 0.18.

The API and a supplemental hydrophobic compound can be co-encapsulated in the nanoparticles. For example, the supplemental hydrophobic compound can be a therapeutic, an imaging agent, or an agrochemical compound.

The API can include gentamycin, polymyxin B, mastoporan 7, sub5, LL37, colistin, ecumicin, OZ439, ovalbumin, or lysozyme. The API can include an antimicrobial small molecule, or example, an antimicrobial small molecule having a molecular weight of less than 1000 Da. The API can include an aminoglycoside, for example, a 4,6-disubstituted deoxystreptamine trisaccharide. The API can include an oligopeptide, such as a linear oligopeptide or a cyclic oligopeptide, which can have a molecular weight of from 1000 Da to 2000 Da. The API can include a protein, such as an anionic protein or a cationic protein, which can have a molecular weight of greater than 2000 Da.

The IP reagent can include sodium dodecyl sulfate (SDS), sodium decyl sulfate (DS), sodium dodecylbenzene sulfonate (DBS), sodium myristate (MA), sodium oleate (OA), pamoic acid disodium salt (PA), vitamin E succinate, or sodium dextran sulfate (DXS). The counterion can include dodecyl hydrogen sulfate, decyl hydrogen sulfate, dodecylbenzene sulfonic acid, myristic acid, oleic acid, pamoic acid, vitamin E succinic acid, or dextran hydrogen sulfate. The counterion can include a fatty acid, an alkyl hydrogen sulfate, an alkylsulfonic acid, or an alkyl quaternary ammonium cation.

The polymer can include hydroxypropyl methylcellulose acetate succinate (HPMCAS), polystyrene-block-polyethylene glycol (PS-b-PEG), or polycaprolactone-block-polyethylene glycol (PCL-b-PEG). The polymer can include a block copolymer, for example an amphiphilic block copolymer. The block copolymer can have a molecular weight of about 10 kDa or less.

DETAILED DESCRIPTION OF THE INVENTION

Figure 1:
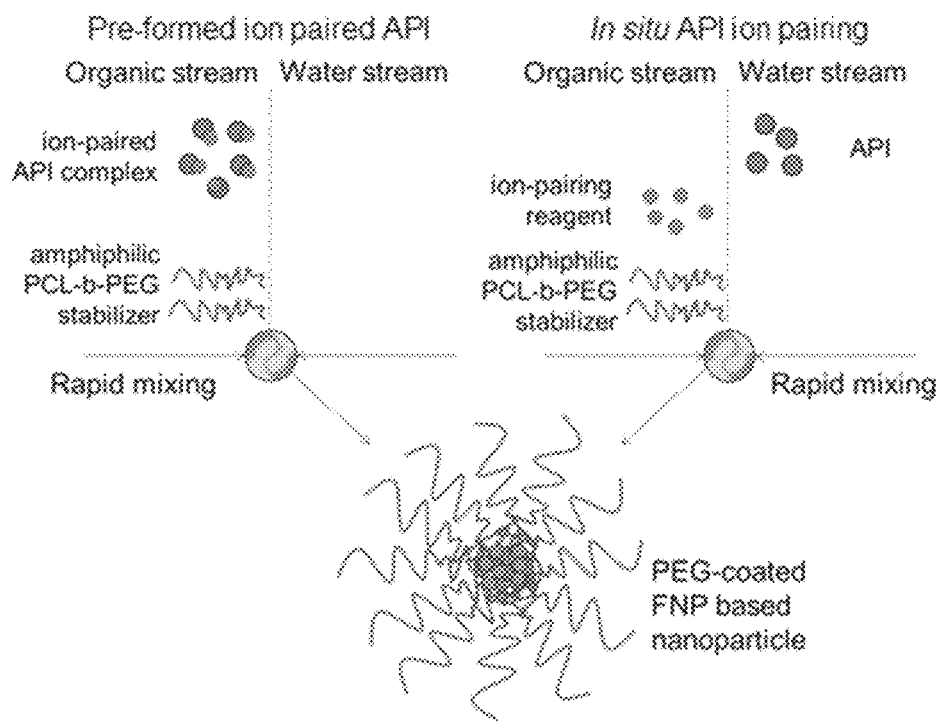
FIG. 1 illustrates the Mechanism of ion pairing-based Flash NanoPrecipitation. FNP of pre-ion paired API. Hydrophilic active pharmaceutical ingredients are created as a hydrophobic salt by pre-pairing the API with a hydrophobic counterion. Pre-ion paired APIs are dissolved in organic solvent alongside an amphiphilic block-copolymer, and rapidly micromixed against water. Hydrophobic API ion pairs precipitate into NCs and self-assemble into NCs. FNP with in situ ion pairing. Hydrophilic APIs are dissolved in water and rapidly micromixed against organic solvent containing a hydrophobic API counterion and an amphiphilic block-copolymer. Ion pairing of the API occurs during mixing, producing a hydrophobic API ion pair that precipitates in the presence of an amphiphilic block-copolymer, resulting in the formation of NCs.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated.

Nanoprecipitation of active pharmaceutical ingredients (APIs) into drug carriers, e.g., to form nanocarriers (NCs), for example, nanoparticles (NPs), can be used to produce formulations with stable nanoparticles and biological efficacy. (In this text, unless otherwise indicated, the terms "nanocarrier" (NC) and "nanoparticle" (NP) are used interchangeably.) However, many nanoprecipitation techniques are applicable for only hydrophobic and water-insoluble APIs, and have not been demonstrated for highly soluble therapeutics. Presented here is a model and technique to encapsulate water-soluble APIs using nanoprecipitation techniques by manipulating API salt forms. APIs are ion paired with hydrophobic counterions to produce new API salts that exhibit altered solubilities suitable for nanoprecipitation processing. Nanocarrier properties, such as stability and release rates, can be tuned by varying ion-pair (IP) molecular structure and ion-pair to API molar ratios. The tools set forth herein can be used to process hydrophilic APIs into nanocarrier systems. The governing rules of ion pair identity, and processing conditions required for successful encapsulation are experimentally determined and assessed with theoretical models. Successful NC, e.g, nanoparticle, formation for the antibiotic polymyxin B can be facilitated with hydrophobicity of the ion pair acid being greater than logP=2 for strong acids and greater than logP=8 for weak acids. Oleic acid with a logP=8, and pKa=5, can be suitable as an ion pair agent, because it is biocompatible and forms ion pair complexes. NC formation from pre-formed, organic soluble ion pairs, can be compared to in situ ion pairs where NCs are made in a single precipitation step. NC properties, such as stability and release rates, can be tuned by varying ion pair molecular structure and ion pair-to-API molar ratios. For polymyxin B, NCs ~100-200 nm in size and with characteristic API release rates over three days were produced. The embodiments of the invention set forth herein represent new tools and demonstrate a new approach that enables the formation of nanoparticles from previously intractable compounds, for example, enabling the processing of hydrophilic APIs into nanocarrier systems.

Thus, set forth herein is encapsulation of hydrophilic actives into nanocarriers via hydrophobic ion-pairing. This approach may be employed, inter alia, in treatment of infectious diseases, such as bacterial, fungal, viral, and parasitic infections. More particularly, the controlled delivery of active therapeutic ingredients (APIs) through nanocarriers can result in improved bioavailability, reduced toxicity, sustained activity, simplified dosing regimens, improved patient adherence, and enhanced overall efficacy.

In a process that is an embodiment of the invention, charged functional groups on the API are ion-paired with a counter ion to produce an API with transiently altered solubilities. Flash NanoPrecipitation (FNP) was used to self-assemble nanoparticles (NPs) containing an encapsulated API-IP complex. Two routes of assembly were explored: (1) complexation of the API with the hydrophobic counterion during FNP (termed "in situ ion pairing"); and (2) complexation prior to FNP (termed "pre-ion pairing"). For the pre-ion paired method, particles were formed by rapid micro-mixing of a hydrophobic-hydrophilic block-copolymer and API-IP complex dissolved in an organic solvent against deionized (DI) water through a confined impingement jet (CIJ) mixer. For the in situ ion-pairing method, the organic stream containing block copolymer and anionic IP dissolved in organic solvent were rapidly micro-mixed with the water stream containing cationic hydrophilic API dissolved in water through a CIJ mixer. For both methods, the organic and water streams were mixed in a 1:1 volume ratio and the resulting mixed streams were subsequently diluted tenfold into water.

In nanoprecipitation processes, APIs may be dissolved in organic solvents and mixed with water as an antisolvent to induce precipitation and nanocarrier self-assembly. However, such direct precipitation methods may be only feasible for water insoluble compounds (cLog P>4), and may not be feasible for encapsulating hydrophilic biologics into nanocarriers. Water soluble biologics may be encapsulated through alternative water-in-oil-in-water emulsion (W/O/W) or liposomal processes that require multiple steps, suffer from poor encapsulation efficiencies, or exhibit low drug mass loadings.

Experimental verification showed the approach of the invention to be capable of encapsulating hydrophilic APIs using Flash NanoPrecipitation via hydrophobic ion pairing. For example, the following APIs were encapsulated: the antimicrobial small molecules polymyxin B and colistin; the peptides mastoparan 7 and sub5; the protein ovalbumin; and the aminoglycoside gentamycin.

The successful formulation of tobramycin, gentamycin, and polymyxin B into NPs with the FNP process can expand the applicability of these therapeutics. For example, these APIs, which are used to manage *P. aeruginosa* bacterial pulmonary cystic fibrosis infections, adhere to pulmonary mucus and do not effectively reach sites of infections after drug administration. Previously, for nanoparticle formulations, the ability to encapsulate soluble APIs and control release had been limited to liposomal formulations; and while some liposomes can be loaded by a mechanism of transfer across the liposome bilayer and precipitation inside the liposome, this technique is not available for highly ionic API's such as the antibiotics considered herein. Therefore, the ion pairing approach presented herein provides a powerful new tool for encapsulation of API's that was not previously available.

Pharmaceutical companies can apply the disclosed technology to enhance drug-based therapies that are already in the market. Pharmaceutical companies can also apply this technology to enable drug therapies to satisfy clinical trial objectives that would be otherwise not met.

The controlled delivery of active therapeutic ingredients from nanocarriers can result in improved bioavailability, reduced toxicity, sustained activity, simplified dosing regimens, improved patient adherence, and enhanced overall efficacy [Solaro, R., F. Chiellini, and A. Battisti, Targeted Delivery of Protein Drugs by Nanocarriers. *Materials*, 2010. 3 (3): p. 1928-1980.]. NC formulations (e.g., nanoparticles) can be used to target delivery, and then to release cargo at the desired site. NC formation through direct precipitation methods is attractive because these methods form NCs, e.g., rapidly form active pharmaceutical ingredient (API) nanoparticles, with high mass loadings in a scalable and continuous fashion, as in the case of Flash NanoPrecipitation (FNP) [Immordino, M. L., F. Dosio, and L. Cattel, Stealth liposomes: review of the basic science, rationale, and clinical applications, existing and potential. *International Journal of Nanomedicine*, 2006. 1 (3): p. 297-315; Steichen, S. D., M. Caldorera-Moore, and N. A. Peppas, A review of current nanoparticle and targeting moieties for the delivery of cancer therapeutics. *European Journal of Pharmaceutical Sciences*, 2013. 48 (3): p. 416-427.; Galindo-Rodriguez, S. A., et al., Polymeric nanoparticles for oral delivery of drugs and vaccines: a critical evaluation of in vivo studies. *Critical Reviews in Therapeutic Drug Carrier Systems*, 2005. 22 (5): p. 419-464.]. In nanoprecipitation processes, APIs, e.g., hydrophobic APIs, may be dissolved in organic solvents and mixed with water as an antisolvent to induce precipitation and NC self-assembly. However, such direct precipitation methods are only feasible for water insoluble compounds (LogP>4), and cannot be used to encapsulate hydrophilic peptides and biologics into NC form. Water soluble biologics may be encapsulated through water-in-oil-in-water emulsion (W/O/W) or liposomal processes that require multiple steps, suffer from poor encapsulation efficiencies, or exhibit low drug mass loadings [Li, S.-D. and L. Huang, Pharmacokinetics and Biodistribution of Nanoparticles. *Molecular Pharmaceutics*, 2008. 5 (4): p. 496-504; Owens Iii, D. E. and N. A. Peppas, Opsonization, biodistribution, and pharmacokinetics of polymeric nanoparticles. *International Journal of Pharmaceutics*, 2006. 307 (1): p. 93-102; Pattni, B. S., V. V. Chupin, and V. P. Torchilin, New Developments in Liposomal Drug Delivery. *Chemical Reviews*, 2015. 115 (19): p. 10938-10966.]. The new methods set forth herein, which efficiently encapsulate hydrophilic APIs into nanocarriers using direct water precipitation methods, can expand the nanocarrier API pharmacokinetic (PK) and/or pharmacodynamics (PD) properties that can be achieved.

Engineering of API water solubilities can enable new processing methods for nanocarrier encapsulation. This can be performed by reversible covalent conjugation of APIs with hydrophobic molecules, which results in the production of a hydrophobic prodrug. After encapsulation and delivery, covalent linkages are cleaved, thereby producing the original API for therapeutic activity. However, covalent modification of APIs results in the creation of a new molecular entity, which requires additional comprehensive, costly, and time-consuming testing for Food & Drug Administration (FDA) approval. API salt form engineering is an alternative route to tune API water solubility. In this process, charged functional groups on the API are ion-paired with a counter ion to produce a API with transiently altered solubilities. An advantage of salt form engineering is that resultant products are not considered new molecular entities, and do not require full FDA reapproval. However, in most instances, API salt forms are screened and engineered for enhanced water solubility. The alternative use of hydrophobic ion-pairs to create hydrophobic salt forms is a non-conventional method to increase API hydrophobicity. This technique has been used for the precipitation of weakly hydrophobic small molecules (cLogP=2-5) into nanocarriers, but not for highly water soluble (cLogP>0) and positively charged biologics. In this text, hydrophobic ion pairing is demonstrated to encapsulate highly soluble, positively charged antibiotic biologics, such as gentamycin (cLogP=−4.21) and polymyxin B (cLogP=−5.6). The ion pairs (IPs) are processed into stable nanocarriers through Flash NanoPrecipitation, a continuous and scalable water precipitation process. A priori, it might have been expected that such biologics could not be precipitated in water with hydrophobic ion-pairs, because of their high API water solubilities. The chemical identities of ion pairs, rules governing precipitation, and processing methods that can give rise to API salts with the desired solubilities for encapsulation were previously unknown.

Previously, ion pairing has been used to formulate nanoparticles from hydrophobic compounds. These are defined by having logP values greater than 1, 2, 3, 4, or 5 at neutral pH [Pinkerton, N. M., et al., Formation of stable nanocarriers by in situ ion pairing during block-copolymer directed rapid precipitation. Molecular pharmaceutics, 2013. 10 (1): p. 319-328]. For example, Song et. al [Song, Y. H., et al., A novel in situ hydrophobic ion pairing (HIP) formulation strategy for clinical product selection of a nanoparticle drug delivery system. Journal of Controlled Release, 2016. 229: p. 106-119.] used ion pairing for AZD281, which had a logP of 2 at a neutral pH of 7. Another group of researchers has complexed proteins and polymeric charged species with oppositely charged polymeric compounds with high solubility. High solubility could mean logP values less than-2 and/or solubilities in aqueous media of over 10 mg/ml at pH=7. Patel and Guadana [Gaudana, R., et al., Design and evaluation of a novel nanoparticulate-based formulation encapsulating a HIP complex of lysozyme. Pharmaceutical development and technology, 2013. 18 (3): p. 752-759; Patel, A., R. Gaudana, and A. K. Mitra, A novel approach for antibody Nanocarriers development through hydrophobic ion-pairing complexation. Journal of Microencapsulation, 2014. 31 (6): p. 542-550] showed that soluble antibody or lysozyme proteins could be complexed with oppositely-charged dextran sulfate. Dextran sulfate is a water-soluble polymer. The resulting precipitate is not a hydrophobic complex, but rather a “coacervate” as commonly defined in the polymer community [Antonov, M., M. Mazzawi, and P. L. Dubin, Entering and exiting the protein-polyelectrolyte coacervate phase via nonmonotonic salt dependence of critical conditions. Biomacromolecules, 2009. 11 (1): p. 51-59; Overbeek, J. T. G. and M. Voorn, Phase separation in polyelectrolyte solutions. Theory of complex coacervation. Journal of Cellular Physiology, 1957. 49 (S1): p. 7-26]. A coacervate is a precipitate resulting from ionic interactions between two soluble polymer species with opposite charges.

Soluble, or relatively soluble, compounds have been encapsulated by covalent conjugation to create hydrophobic pro-drugs [Bruno, B. J., G. D. Miller, and C. S. Lim, Basics and recent advances in peptide and protein drug delivery. *Therapeutic delivery,* 2013. 4 (11): p. 1443-1467.; Jain, A., et al., Peptide and Protein Delivery Using New Drug Delivery Systems. *Crit Rev Ther Drug Carrier Syst.* 2013. 30 (4): p. 293-329.]. After encapsulation and delivery, covalent linkages are cleaved, thereby producing the original API for therapeutic activity. However, covalent modification of APIs results in the creation of a new molecular entity, which requires additional FDA approval. An alternative route to reduce API water solubility is to ion pair the active with a hydrophobic counterion [Muheem, A., et al., A review on the strategies for oral delivery of proteins and peptides and their clinical perspectives. *Saudi Pharmaceutical Journal*, 2016. 24 (4): p. 413-428.; Sohn, J. S., et al., Polymer prodrug approaches applied to paclitaxel. *Polymer Chemistry*, 2010. 1 (6): p. 778-792.; Ansell, S. M., et al., Modulating the Therapeutic Activity of Nanoparticle Delivered Paclitaxel by Manipulating the Hydrophobicity of Prodrug Conjugates. *Journal of Medicinal Chemistry*, 2008. 51 (11): p. 3288-3296.; Marcus, Y. and G. Hefter, Ion Pairing. *Chemical Reviews*, 2006. 106 (11): p. 4585-4621.; Matschiner, S., R. Neubert, and W. Wohlrab, Optimization of topical erythromycin formulations by ion pairing. *Skin Pharmacology: The Official Journal of the Skin Pharmacology Society*, 1995. 8 (6): p. 319-325.]. With this approach the resultant products are not considered new molecular entities and do not require full FDA reapproval. In most instances, API salt forms have been engineered for enhanced water solubility or crystal stability; that is, the technique has been conventionally used for the precipitation of hydrophobic small molecules (LogP=2-5) into NCs. [Serajuddin, A. T. M., Salt formation to improve drug solubility. *Advanced Drug Delivery Reviews*, 2007. 59 (7): p. 603-616.; Meyer, J. D. and M. C. Manning, Hydrophobic Ion Pairing: Altering the Solubility Properties of Biomolecules. *Pharmaceutical Research*, 1998. 15 (2): p. 188-193.]. By contrast, the use of hydrophobic ion pairs to create less soluble drug forms is nonconventional.

In this text is demonstrated hydrophobic ion pairing to encapsulate highly soluble, positively charged antibiotic biologics: using model gentamycin (cLogP=−4.21) and polymyxin B (cLogP=−5.6). The ion pairs are processed into stable nanocarriers through Flash NanoPrecipitation, a continuous and scalable water precipitation process. A priori, it might have been expected that such biologics cannot be precipitated in water with hydrophobic ion pairs, because of their high water solubilities. The chemical identities of ion pairs, rules governing precipitation, and processing methods that can give rise to API salts with the desired solubilities for encapsulation were previously unknown.

This text describes the use of Flash NanoPrecipitation, a continuous and scalable method of forming NCs with high API mass loads (>50 to 90%) to encapsulate the APIs. The FNP process relies upon rapid micromixing (O (ms)) of a solvent and an antisolvent stream to create high supersaturations, which drive high nucleation rates. The hydrophobic APIs precipitate into NCs, while the hydrophobic block of the stabilizing polymer absorbs onto the NC surface to arrest particle growth. This results in highly loaded NCs with a narrow size distribution. We have described the process in detail elsewhere [Johnson, B. K. and R. K. Prud'homme, Flash NanoPrecipitation of Organic Actives and Block Copolymers using a Confined Impinging Jets Mixer. *Australian Journal of Chemistry*, 2003. 56 (10): p. 1021-1024.; D'Addio, S. M. and R. K. Prud'homme, Controlling drug nanoparticle formation by rapid precipitation. *Advanced Drug Delivery Reviews*, 2011. 63 (6): p. 417-426.; Saad, W. S. and R. K. Prud'homme, Principles of nanoparticle formation by flash nanoprecipitation. *Nano Today*, 2016. 11 (2): p. 212-227.].

Certain research has considered the precipitation of oligonucleotides (DNA, RNA, siRNA, mRNA) with oppositely-charged hydrophobic lipids [Gindy, M. E., et al., Mechanism of macromolecular structure evolution in self-assembled lipid nanoparticles for siRNA delivery. *Langmuir*, 2014. 30 (16): p. 4613-4622.; Luo, D. and W. M. Saltzman, Synthetic DNA delivery systems. *Nature biotechnology*, 2000. 18 (1): p. 33-37.; Mueller, R. H., K. Maeder, and S. Gohla, Solid lipid nanoparticles (SLN) for controlled drug delivery—a review of the state of the art. *European journal of pharmaceutics and biopharmaceutics*, 2000. 50 (1): p. 161-177.; Rädler, J. O., et al., Structure of DNA-cationic liposome complexes: DNA intercalation in multilamellar membranes in distinct interhelical packing regimes. *Science*, 1997. 275 (5301): p. 810-814.]. These examples are only demonstrated for complexation with the highly negatively charged oligonucleotides which have charge spacings of 3.4 Å, which is for 6 bonds between ionized phosphorous units. Prior to the invention in this patent application there was no indication that materials with lower charge densities than oligonucleotides could be precipitated with hydrophobic compounds to produce nanoparticles.

The ion pairing between the highly soluble active species (API) and the counterion species can form nanoparticles using either the Flash NanoPrecipitation technique or an emulsification and stripping technique [Song, Y. H., et al., A novel in situ hydrophobic ion pairing (HIP) formulation strategy for clinical product selection of a nanoparticle drug delivery system. Journal of Controlled Release, 2016. 229: p. 106-119]. The nanoparticles formed can, for example, have sizes between 25 nm and 100 nm, or 25 nm and 400 nm, or 25 nm and 1000 nm, or 25 nm and 1200 nm, or 25 nm and 6000 nm. Sizes can be measured using a Malvern Nanosizer dynamic light scattering instrument using normal mode analysis software. The Z-average, also known as intensity average, diameter is reported.

The ion pairing process described herein can be useful for the preparation of antibacterial actives. Antibacterial agents based on peptide units can be suitable for this ion pairing technique.

Embodiments according to the present invention can include the complexation of highly soluble actives, that is, the species of interest to be encapsulated, with oppositely charged hydrophobic species.

An embodiment of the invention involves the complexation of highly soluble actives, that is, the species of interest to be encapsulated, with oppositely-charged hydrophobic species. For example, the actives can have solubilities of greater than 10 mg/ml or logP values of −2 or less or −3 or less in pH 7 aqueous solutions. The actives (APIs) can have 2, 3, 4, 5, 6, or more ionic groups that make them water soluble. In an embodiment, the actives can be other than oligonucleotides.

In an embodiment of the invention, an active of intermediate solubility, e.g., −2<logP<5, can be ion paired with a hydrophobic counterion, so that the formed complex precipitates in a mixing step in FNP and is encapsulated in a NP.

The use of ion pairing agents with logP values greater than 5 can be useful in making encapsulated actives with release profiles that include a plateau in release rates (release over time).

In an embodiment, the counterions that cause precipitation can have logP values of 2 or greater at pH=7. In an embodiment, the counterions can have 1, 2, or more ionic sites. In an embodiment, anionic counterions can have pKa values of −2 to 5. In an embodiment, the counterions can have pKb values above 3, or may be quaternized cationic species that are permanently cationic. In an embodiment, the ionic sites may be carboxylic acids, sulfates, sulfonates, sulfates, or amines.

Oleic and palmitic acids can be useful ion-pairing agents or counterions for an embodiment of the invention.

The ion paired hydrophilic active may be co-encapsulated along with a hydrophobic compound, such as a therapeutic, imaging agent, or agrochemical.

The successful formulation of therapeutics such as tobramycin and polymyxin B into NPs with the FNP process can expand their applicability. These APIs, which are used to manage *P. aeruginosa* bacterial pulmonary cystic fibrosis infections, adhere to pulmonary mucus and do not effectively reach sites of infections after drug administration [Davies, J. C., A.-M. Ebdon, and C. Orchard, Recent advances in the management of cystic fibrosis. *Archives of Disease in Childhood*, 2014. 99 (11): p. 1033-1036.; Lai, S. K., et al., Rapid transport of large polymeric nanoparticles in fresh undiluted human mucus. *Proceedings of the National Academy of Sciences*, 2007. 104 (5): p. 1482-1487.]. To mitigate this effect, APIs can be encapsulated into mucus-penetrating vehicles for delivery [Muheem, A., et al., A review on the strategies for oral delivery of proteins and peptides and their clinical perspectives. *Saudi Pharmaceutical Journal*, 2016. 24 (4): p. 413-428.; Sohn, J. S., et al., Polymer prodrug approaches applied to paclitaxel. *Polymer Chemistry*, 2010. 1 (6): p. 778-792.; Ensign, L. M., R. Cone, and J. Hanes, Oral drug delivery with polymeric nanoparticles: The gastrointestinal mucus barriers. *Advanced Drug Delivery Reviews*, 2012. 64 (6): p. 557-570.; Lai, S. K., Y.-Y. Wang, and J. Hanes, Mucus-penetrating nanoparticles for drug and gene delivery to mucosal tissues. *Advanced drug delivery reviews*, 2009. 61 (2): p. 158-171.; Khanvilkar, K., M. D. Donovan, and D. R. Flanagan, Drug transfer through mucus. *Advanced Drug Delivery Reviews*, 2001. 48 (2-3): p. 173-193.; Cu, Y. and W. M. Saltzman, Drug delivery: Stealth particles give mucus the slip. *Nature Materials*, 2009. 8 (1): p. 11-13.; Livraghi, A. and S. H. Randell, Cystic Fibrosis and Other Respiratory Diseases of Impaired Mucus Clearance. *Toxicologic Pathology*, 2007. 35 (1): p. 116-129.]. However, liposomal formulations suffer from poor drug loading, as the drugs are limited to within the water interior of the construct. Poor drug loadings and the high costs of liposomal antibiotic formulation processes pose a significant barrier for widespread adoption, since antibiotic therapies are priced low relative to cancer therapies that utilize liposomal formulations. In contrast, FNP is a continuous and scalable method of forming NPs with high API mass loads (>50-90%) using kinetic controlled self-assembly [Høiby, N., Recent advances in the treatment of *Pseudomonas aeruginosa* infections in cystic fibrosis. BMC Medicine, 2011. 9: p. 32-32.; Davies, J. C., A.-M. Ebdon, and C. Orchard, Recent advances in the management of cystic fibrosis. *Archives of Disease in Childhood*, 2014. 99 (11): p. 1033-1036.; Lai, S. K., et al., Rapid transport of large polymeric nanoparticles in fresh undiluted human mucus. *Proceedings of the National Academy of Sciences*, 2007. 104 (5): p. 1482-1487.]. Hydrophobic APIs and amphiphilic block copolymers can be dissolved in a water miscible organic stream, and rapidly mixed with water within a confined impingement jet (CIJ) mixer. Hydrophobic APIs precipitate into nanoparticles, while the hydrophobic block of the polymer absorbs onto API NPs to arrest particle growth into a defined diameter and narrow size distribution. The hydrophilic component of the block copolymer provides a steric stabilizing layer and affords water dispersity. If a polyethylene glycol (PEG) hydrophilic functionalized block copolymer is used during FNP, particles can exhibit mucus-penetrating properties. [Crater, J. S. and R. L. Carrier, Barrier Properties of Gastrointestinal Mucus to Nanoparticle Transport. *Macromolecular Bioscience*, 2010. 10 (12): p. 1473-1483.] The development of a new FNP-based process to encapsulate hydrophilic APIs, including biologics such as antibiotics, would expand the types of applications for which such hydrophilic biologics can be used.

The ion pairs (IPs) can be processed into stable NCs through Flash NanoPrecipitation (FNP). The ion pairing technique is quite general, but as examples, we show gentamicin (LogP=−4.21) and polymyxin B (LogP=−5.6). These cationic APIs, which are used to manage *P. aeruginosa* bacterial pulmonary cystic fibrosis infections, adhere to pulmonary mucus and do not effectively reach sites of infections after drug administration [Langer, R., Drug delivery and targeting. Nature, 1998. 392 (6679): p. 5-10.; Zhang, L., et al., Development of Nanoparticles for Antimicrobial Drug Delivery. *Current Medicinal Chemistry*, 2010. 17 (6): p. 585-594.]. Encapsulation, especially in a muco-diffusive PEG NC would increase efficacy.

EXPERIMENTAL EXAMPLES

Sodium hexanoate, sodium decanoate, sodium myristate, sodium oleate (OA), pamoic acid disodium salt (PA), benzenesulfonic acid monohydrate, sodium 2-naphthalenesulfonate, (1R)-(−)-10-camphorsulfonic acid, sodium 1,2-ethanesulfonate, sodium 1-heptanesulfonate, sodium 1-octanesulfonate monohydrate, sodium 1-decanesulfonate, sodium dodecyl sulfate (SDS), sodium dodecylbenezenesulfonate (DBS), and sodium deoxycholate were obtained from Sigma-Aldrich (St. Louis, MO, USA) and used as ion pairing reagents. Gentamicin sulfate (MP Biochemicals, Santa Ana, California, USA) and polymyxin B sulfate (Calbiochem, San Diego, CA, USA) were used as hydrophilic and cationic antibiotic APIs for encapsulation. The block copolymers 1.6 kDa polystyrene-block-5 kDa polyethylene glycol (abbreviated herein as PS-PEG, PS-b-PEG, or PS1.6k-b-PEG5k) and 5 kDa polycaprolactone-block-5 kDa polyethylene glycol (abbreviated herein as PCL-PEG, PCL-b-PEG, or PCL5k-b-PEG5k) were obtained from Polymersource (Montreal, Quebec, Canada) and used as NC formation, encapsulation, and stabilizing agents. Bicinchoninic acid (BCA) assay reagents were obtained from Thermo Scientific (Waltham, MA, USA) and used to quantify protein concentrations. Corning 96 well, clear, circular flat bottom, half area microplates were used for the BCA assays. Amicon 50 kDa centrifugal ultrafilters (EMD Millipore, Billerica, MA, USA) were used to separate encapsulated drug from unencapsulated drugs.

Ion Pairing Screening

The fifteen ion pairing (IP) reagents listed above were screened to assess if hydrophobic API salt forms would be formed and would precipitate from solution. Ion pair and API drug properties were calculated with Molinspiration software (Molinspiration Cheminformatics, Slovakia). APIs were dissolved in water at 5 mg mL$^{-1}$ concentration and mixed with IPs dissolved in water at varying concentrations to yield different API to IP ratios. Ratios are defined based on positive charges of APIs with negative charges on the IP, and exact compositions given in Table 1. The screening process determines whether a particular IP may be used with a given API for NC formation.

TABLE 1

Summary of nanoparticles formed with ion-pairing based Flash NanoPrecipitation.
Nanoparticle properties are determined with dynamic light scattering analysis. Values are
averages and error bars are standard deviations of three measurements.

| | | | Stabilizer | | Co-core | | Active Core | | NP Properties | |
|---|---|---|---|---|---|---|---|---|---|---|
| # | Method | Formulation Name | Block Copolymer | Conc (mg/mL) | Ion-Pair | Conc (mg/mL) | API | Conc (mg/mL) | Z-Diameter (nm) | PDI |
| 1 | Pre-paired | 1:0.5 polymyxin:SDS | $PCL_{3.9k}$-b-$PEG_{5k}$ | 5.0 | SDS | 2.8 | Polymyxin | 5.0 | 144 ± 1 | .13 ± .02 |
| 2 | Pre-paired | 1:1 polymyxin:SDS | $PCL_{3.9k}$-b-$PEG_{5k}$ | 5.0 | SDS | 5.5 | Polymyxin | 5.0 | 192 ± 3 | .12 ± .04 |
| 3 | Pre-paired | 1:2 polymyxin:SDS | $PCL_{3.9k}$-b-$PEG_{5k}$ | 5.0 | SDS | 11.1 | Polymyxin | 5.0 | 147 ± 4 | .10 ± .01 |
| 4 | Pre-paired | 1:4 polymyxin:SDS | $PCL_{3.9k}$-b-$PEG_{5k}$ | 5.0 | SDS | 22.2 | Polymyxin | 5.0 | 96 ± 1 | .13 ± .02 |
| 5 | Pre-paired | 1:0.5 gentamicin:SDS | $PCL_{3.9k}$-b-$PEG_{5k}$ | 5.0 | SDS | 2.8 | Gentamicin | 2.3 | 153 ± 0 | .08 ± .02 |
| 6 | Pre-paired | 1:1 gentamicin:SDS | $PCL_{3.9k}$-b-$PEG_{5k}$ | 5.0 | SDS | 5.5 | Gentamicin | 2.3 | 201 ± 5 | .18 ± .04 |
| 7 | Pre-paired | 1:2 gentamicin:SDS | $PCL_{3.9k}$-b-$PEG_{5k}$ | 5.0 | SDS | 11.1 | Gentamicin | 2.3 | 138 ± 1 | .08 ± .05 |
| 8 | Pre-paired | 1:4 gentamicin:SDS | $PCL_{3.9k}$-b-$PEG_{5k}$ | 5.0 | SDS | 22.2 | Gentamicin | 2.3 | 86 ± 2 | .22 ± .02 |
| 9 | Pre-paired | 1:0.5 polymyxin:PA | $PS_{1.6k}$-b-$PEG_{5k}$ | 5.0 | PA | 2.1 | Polymyxin | 5.0 | 101 ± 3 | .13 ± .01 |
| 10 | Pre-paired | 1:1 polymyxin:PA | $PS_{1.6k}$-b-$PEG_{5k}$ | 5.0 | PA | 4.2 | Polymyxin | 5.0 | 112 ± 0 | .08 ± .06 |
| 11 | Pre-paired | 1:2 polymyxin:PA | $PS_{1.6k}$-b-$PEG_{5k}$ | 5.0 | PA | 8.3 | Polymyxin | 5.0 | 792 ± 35 | .12 ± .06 |
| 12 | Pre-paired | 1:4 polymyxin:PA | $PS_{1.6k}$-b-$PEG_{5k}$ | 5.0 | PA | 16.6 | Polymyxin | 5.0 | 751 ± 35 | .24 ± .12 |
| 13 | Pre-paired | 1:0.5 gentamicin:PA | $PS_{1.6k}$-b-$PEG_{5k}$ | 5.0 | PA | 2.1 | Gentamicin | 2.3 | 48 ± 23 | .26 ± .03 |
| 14 | Pre-paired | 1:1 gentamicin:PA | $PS_{1.6k}$-b-$PEG_{5k}$ | 5.0 | PA | 4.2 | Gentamicin | 2.3 | 63 ± 32 | .24 ± .06 |
| 15 | Pre-paired | 1:2 gentamicin:PA | $PS_{1.6k}$-b-$PEG_{5k}$ | 5.0 | PA | 8.3 | Gentamicin | 2.3 | 94 ± 1 | .08 ± .02 |
| 16 | Pre-paired | 1:4 gentamicin:PA | $PS_{1.6k}$-b-$PEG_{5k}$ | 5.0 | PA | 16.6 | Gentamicin | 2.3 | 107 ± 1 | .09 ± .01 |
| 17 | Pre-paired | 1:1 polymyxin:DBS | $PCL_{3.9k}$-b-$PEG_{5k}$ | 5.0 | DBS | 6.7 | Polymyxin | 5.0 | 151 ± 2 | .07 ± .06 |
| 18 | Pre-paired | 1:2 polymyxin:DBS | $PCL_{3.9k}$-b-$PEG_{5k}$ | 5.0 | DBS | 13.4 | Polymyxin | 5.0 | 158 ± 1 | .13 ± .01 |
| 19 | Pre-paired | 1:1 gentamicin:DBS | $PCL_{3.9k}$-b-$PEG_{5k}$ | 5.0 | DBS | 6.7 | Gentamicin | 2.3 | 153 ± 3 | .06 ± .04 |
| 20 | Pre-paired | 1:2 gentamicin:DBS | $PCL_{3.9k}$-b-$PEG_{5k}$ | 5.0 | DBS | 13.4 | Gentamicin | 2.3 | 111 ± 2 | .13 ± .02 |
| 21 | Pre-paired | 1:1 polymyxin:DS | $PCL_{3.9k}$-b-$PEG_{5k}$ | 5.0 | DS | 4.7 | Polymyxin | 5.0 | 119 ± 1 | .16 ± .01 |
| 22 | Pre-paired | 1:2 polymyxin:DS | $PCL_{3.9k}$-b-$PEG_{5k}$ | 5.0 | DS | 9.4 | Polymyxin | 5.0 | 157 ± 5 | .11 ± .03 |
| 23 | Pre-paired | 1:1 gentamicin:DS | $PCL_{3.9k}$-b-$PEG_{5k}$ | 5.0 | DS | 4.7 | Gentamicin | 2.3 | 72 ± 2 | .12 ± .03 |
| 24 | Pre-paired | 1:2 gentamicin:DS | $PCL_{3.9k}$-b-$PEG_{5k}$ | 5.0 | DS | 9.4 | Gentamicin | 2.3 | 96 ± 4 | .22 ± .02 |
| 25 | In-situ | 1:0.5 polymyxin:SDS | $PCL_{3.9k}$-b-$PEG_{5k}$ | 5.0 | SDS | 2.8 | Polymyxin | 5.0 | 188 ± 4 | .13 ± .06 |
| 26 | In-situ | 1:1 polymyxin:SDS | $PCL_{3.9k}$-b-$PEG_{5k}$ | 5.0 | SDS | 5.5 | Polymyxin | 5.0 | 158 ± 3 | .04 ± .02 |
| 27 | In-situ | 1:2 polymyxin:SDS | $PCL_{3.9k}$-b-$PEG_{5k}$ | 5.0 | SDS | 11.1 | Polymyxin | 5.0 | 127 ± 3 | .08 ± .05 |
| 28 | In-situ | 1:4 polymyxin:SDS | $PCL_{3.9k}$-b-$PEG_{5k}$ | 5.0 | SDS | 22.2 | Polymyxin | 5.0 | 117 ± 2 | .12 ± .01 |
| 29 | In-situ | 0:1 polymyxin:SDS control | $PCL_{3.9k}$-b-$PEG_{5k}$ | 5.0 | SDS | 5.5 | Polymyxin | 0.0 | 52 ± 12 | .19 ± .05 |
| 30 | In-situ | 1:0.5 polymyxin:DS | $PCL_{3.9k}$-b-$PEG_{5k}$ | 5.0 | DS | 2.3 | Polymyxin | 5.0 | 50 ± 0 | .21 ± .01 |
| 31 | In-situ | 1:1 polymyxin:DS | $PCL_{3.9k}$-b-$PEG_{5k}$ | 5.0 | DS | 4.7 | Polymyxin | 5.0 | 47 ± 0 | .19 ± .02 |
| 32 | In-situ | 1:2 polymyxin:DS | $PCL_{3.9k}$-b-$PEG_{5k}$ | 5.0 | DS | 9.4 | Polymyxin | 5.0 | 59 ± 3 | .34 ± .01 |
| 33 | In-situ | 1:4 polymyxin:DS | $PCL_{3.9k}$-b-$PEG_{5k}$ | 5.0 | DS | 18.8 | Polymyxin | 5.0 | 168 ± 8 | .08 ± .01 |
| 34 | In-situ | 0:1 polymyxin:DS control | $PCL_{3.9k}$-b-$PEG_{5k}$ | 5.0 | DS | 4.7 | Polymyxin | 0.0 | 62 ± 24 | .19 ± .05 |
| 35 | In-situ | 1:0.5 polymyxin:DBS | $PCL_{3.9k}$-b-$PEG_{5k}$ | 5.0 | DBS | 3.3 | Polymyxin | 5.0 | 122 ± 1 | .16 ± .04 |
| 36 | In-situ | 1:1 polymyxin:DBS | $PCL_{3.9k}$-b-$PEG_{5k}$ | 5.0 | DBS | 6.7 | Polymyxin | 5.0 | 133 ± 3 | .10 ± .03 |
| 37 | In-situ | 1:2 polymyxin:DBS | $PCL_{3.9k}$-b-$PEG_{5k}$ | 5.0 | DBS | 13.4 | Polymyxin | 5.0 | 97 ± 2 | .13 ± .04 |
| 38 | In-situ | 1:4 polymyxin:DBS | $PCL_{3.9k}$-b-$PEG_{5k}$ | 5.0 | DBS | 26.8 | Polymyxin | 5.0 | 120 ± 2 | .15 ± .04 |
| 39 | In-situ | 0:1 polymyxin:DBS control | $PCL_{3.9k}$-b-$PEG_{5k}$ | 5.0 | DBS | 6.7 | Polymyxin | 0.0 | 57 ± 20 | .50 ± .25 |
| 40 | In-situ | 1:0.5 polymyxin:OA | $PCL_{3.9k}$-b-$PEG_{5k}$ | 5.0 | OA | 2.9 | Polymyxin | 5.0 | 146 ± 1 | .07 ± .03 |
| 41 | In-situ | 1:1 polymyxin:OA | $PCL_{3.9k}$-b-$PEG_{5k}$ | 5.0 | OA | 5.9 | Polymyxin | 5.0 | 130 ± 0 | .06 ± .02 |
| 42 | In-situ | 1:2 polymyxin:OA | $PCL_{3.9k}$-b-$PEG_{5k}$ | 5.0 | OA | 11.7 | Polymyxin | 5.0 | 103 ± 2 | .08 ± .03 |
| 43 | In-situ | 1:4 polymyxin:OA | $PCL_{3.9k}$-b-$PEG_{5k}$ | 5.0 | OA | 23.4 | Polymyxin | 5.0 | 119 ± 2 | .07 ± .04 |
| 44 | In-situ | 0:1 polymyxin:OA control | $PCL_{3.9k}$-b-$PEG_{5k}$ | 5.0 | OA | 5.9 | Polymyxin | 0.0 | 150 ± 2 | .27 ± .02 |
| 45 | In-situ | 1:0.5 polymyxin:MA | $PCL_{3.9k}$-b-$PEG_{5k}$ | 5.0 | MA | 2.4 | Polymyxin | 5.0 | 168 ± 3 | .10 ± .03 |
| 46 | In-situ | 1:1 polymyxin:MA | $PCL_{3.9k}$-b-$PEG_{5k}$ | 5.0 | MA | 4.8 | Polymyxin | 5.0 | 140 ± 5 | .07 ± .03 |
| 47 | In-situ | 1:2 polymyxin:MA | $PCL_{3.9k}$-b-$PEG_{5k}$ | 5.0 | MA | 9.6 | Polymyxin | 5.0 | 121 ± 2 | .07 ± .02 |
| 48 | In-situ | 1:4 polymyxin:MA | $PCL_{3.9k}$-b-$PEG_{5k}$ | 5.0 | MA | 19.2 | Polymyxin | 5.0 | 96 ± 2 | .17 ± .00 |
| 49 | In-situ | 0:1 polymyxin:MA control | $PCL_{3.9k}$-b-$PEG_{5k}$ | 5.0 | MA | 4.8 | Polymyxin | 0.0 | 2144 ± 1097 | 1 ± 0 |
| 50 | In-situ | 1:0.5 polymyxin:PA | $PCL_{3.9k}$-b-$PEG_{5k}$ | 5.0 | PA | 2.1 | Polymyxin | 5.0 | 70 ± 1 | .23 ± .01 |
| 51 | In-situ | 1:1 polymyxin:PA | $PCL_{3.9k}$-b-$PEG_{5k}$ | 5.0 | PA | 4.2 | Polymyxin | 5.0 | 75 ± 1 | .15 ± .01 |
| 52 | In-situ | 1:2 polymyxin:PA | $PCL_{3.9k}$-b-$PEG_{5k}$ | 5.0 | PA | 8.3 | Polymyxin | 5.0 | 96 ± 0 | .21 ± .01 |
| 53 | In-situ | 1:4 polymyxin:PA | $PCL_{3.9k}$-b-$PEG_{5k}$ | 5.0 | PA | 16.6 | Polymyxin | 5.0 | 80 ± 1 | .22 ± .01 |
| 54 | In-situ | 0:1 polymyxin:PA control | $PCL_{3.9k}$-b-$PEG_{5k}$ | 5.0 | PA | 4.2 | Polymyxin | 0.0 | 49 ± 1 | .12 ± .04 |
| 55 | In-situ | 50% DMSO/THF no IP | $PCL_{3.9k}$-b-$PEG_{5k}$ | 5.0 | none | 0.0 | Polymyxin | 5.0 | 50 ± 2 | .14 ± .04 |
| 56 | In-situ | 50% MeOH/THF no IP | $PCL_{3.9k}$-b-$PEG_{5k}$ | 5.0 | none | 0.0 | Polymyxin | 5.0 | 349 ± 524 | .58 ± .25 |
| 57 | In-situ | 20% water/80% THF no IP | $PCL_{3.9k}$-b-$PEG_{5k}$ | 5.0 | none | 0.0 | Polymyxin | 5.0 | 74 ± 14 | .52 ± .12 |
| 58 | In-situ | 0:1 polymyxin:DCL control | $PCL_{3.9k}$-b-$PEG_{5k}$ | 5.0 | DCL | 8.0 | Polymyxin | 5.0 | 46 ± 2 | .41 ± .01 |

The IP process may be performed either prior to or during Flash NanoPrecipitation. In the case of the latter, referred to as "in situ ion pairing" or "pre-ion pairing". These two ion pairing methods are described in FIG. 1. IP and API are mixed in water to form a water-insoluble precipitate (referred to as an API:IP complex). The water is then removed, and the IP-API complex is dissolved into an organic solvent (along with a block copolymer) for use in the organic stream in FNP. In the case of the latter, referred to as "in situ ion pairing", the API and IP are dissolved in the water and organic streams of FNP, respectively, and form the API:IP complex during the rapid micromixing step of FNP. These two ion-pairing methods are described and compared in greater detail below.

Pre-Ion Paired APIs

In the case of pre-ion pairing, API and IP are mixed in water to form a water-insoluble precipitate (referred to as an API:IP complex). The water is then removed, and the API:IP complex is dissolved into an organic solvent (along with a block copolymer) for use in the organic stream in FNP. In this case, the API:IP complex is treated as a component in the organic stream of normal FNP. The screening process for the pre-ion paired method FNP involves four sequential tests.

1. The first test examines the solubility of the IP agent. IP is added to DI water at a concentration that would be required for a 1:1 API:IP charge ratio if the API were dissolved at 5 mg mL$^{-1}$. (In this text the ratios are presented as charge ratios of API:IP.) Substantial insolubility in water is required for successful ion pairing.
2. The second test examines whether an in situ API:IP complex can be formed in a single step. For example, The second test examines whether solids precipitate upon mixing of the aqueous IP solution with an aqueous API solution. Alternatively, IP in an organic, but water miscible, solution is mixed against the aqueous API solution. The final solution is checked visually to see if precipitation has occurred. In this test, the IP solution is at a concentration such that mixing equal volumes of IP solution and API solution will form a 1:1 API to IP charge ratio. Four API:IP ratios are investigated: 200 μL API solution is mixed with 100 μL IP solution for a 1:0.5 charge ratio; 200 μL API solution is mixed with 200 μL IP solution for a 1:1 charge ratio; 200 μL API solution is mixed with 400 μL IP solution for a 1:2 charge ratio; and 200 μL API solution is mixed with 800 μL IP solution for a 1:4 charge ratio.
3. The third test examines whether the API:IP complex can be solubilized in the organic phase for subsequent FNP NC formation. Pellets of the precipitate formed in the second test are tested to see if they are soluble in a water-miscible organic solvent such as tetrahydrofuran (THF) or more polar solvents such as dimethyl sulfoxide (DMSO) or methanol (MeOH). For example, if precipitates were formed in the second test, the mixture can be centrifuged at 20800 rcf for 20 minutes, and the aqueous supernatant can be removed in order to recover pelleted precipitate. 200 μL of organic solvent can be added to the pellet; the solution can then be mixed to determine whether the pellet dissolves.
4. The final (fourth) test assesses if the hydrophobic API:IP complex will re-precipitates when mixed with water, e.g., upon FNP mixing with water as the anti-solvent. The organic solvent containing API:IP from the third test is diluted ten-fold in water, and precipitate formation is examined. If a precipitate forms, then the construct is suitable for use in FNP.

In Situ Ion Pairing

In this route, the ion pairing complexation occurs in situ, during FNP. The hydrophilic API enters in the aqueous stream, and the stabilizing block copolymer and hydrophobic IP enter in via the water-miscible organic stream. The results of the solubility screening show three different solvent compositions for six IPs. Pamoic acid (PA), sodium dodecyl sulfate (SDS), and sodium decyl sulfate (DS) dissolve in 50% dimethylsulfoxide (DMSO)/tetrahydrofuran (THF); oleic acid (OA) and myristic acid (MA) dissolve in 50% methanol (MeOH)/THF; and sodium dodecylbenzene sulfonate (DBS) dissolves in 20% water/THF.

Nanocarrier Formation by Flash NanoPrecipitation (Ion Pairing of API:IP into PEG-Coated NPs)

Flash NanoPrecipitation was used to self-assemble PEG-coated NCs containing an encapsulated API:IP complex. For the pre-ion paired method, particles were formed by rapid micro-mixing of hydrophobic-hydrophilic block-copolymer PCL-PEG and API:IP complex dissolved in organic solvent against deionized (DI) water through a confined impingement jet (CIJ) mixer. For the in situ ion pairing method, the organic stream containing PCL-PEG and anionic IP dissolved in organic solvent were rapidly micro-mixed in the CIJ mixer against the water stream containing cationic hydrophilic API dissolved in water. For both methods, the organic and water streams were mixed in a 1:1 volume ratio and the resulting mixed streams were subsequently diluted tenfold into water. Concentrations of PCL-PEG stabilizer and hydrophilic API (gentamicin and polymyxin B) were kept constant, while IP concentrations were varied to form NCs, e.g., nanoparticles, with a range of drug (API): IP ratios. This ratio is the ratio of the molar concentration of cationic functional groups in the API, to the molar concentration of anionic functional groups in the IP. Exact compositions of the stabilizer block co-polymers, APIs, and IPs used are given in Table 1 (above).

Nanocarrier Characterization

Particle sizes and polydispersities were characterized by dynamic light scattering (Malvern Zetasizer Nano, Malvern Instruments). Sizes were determined with backscattering measurements and reported as Z-average and intensity-weighted distributions. The polydispersity index (PDI) reported herein is obtained from the Taylor series expansion of the autocorrelation function and is implemented into the Malvern Nanosizer data analysis software. A ratio of the second to the first moment is defined as the PDI, where values of 0.1 are generally obtained for monodisperse particles.

Particles were diluted tenfold into two different collection buffers, deionized (DI) water and 1× phosphate-buffered saline (PBS) for sizing measurements and NC, e.g., nanoparticle, stability assessments. PBS contains significant salt concentration, has an ionic strength of 163 mM, and mimics the ionic strength of serum. Incubation in PBS assesses the stability of the NC under conditions where ion exchange, e.g. with physiological charged species, might destabilize the NC ion-paired complex. NC stability was assessed by taking DLS measurements of the particles at 4 time points: t=0, 3 hr, 24 hr, and 72 hr. Stability measurements were conducted at room temperature.

NC drug encapsulation efficiencies were determined by separating encapsulated API from dissolved/unencapsulated drugs in the NC sample through ultrafiltration across a 50 kDa membrane (Amicon Ultra, EMD Millipore) and determining the concentration of dissolved/unencapsulated API in ultrafiltration flow-through. Encapsulation efficiency is calculated as the concentration of API within the flow-through fraction divided by the concentration of API within the unseparated NC sample, and then subtracting this ratio from 1 (Eq. 1).

Drug concentrations were determined with the bicinchoninic acid (BCA) assay (Spectramax i3x, Molecular Devices) with absorbance measurements at 562 nm, using a standard curve of the same drug (unencapsulated) as the reference. API fractional release was determined by dialyzing NC sample in 100-fold 1×PBS. Aliquots were taken from within the dialysis bag at different time points: t=0, 1 day, 2 days, 3 days, 5 days, and 7 days. The drug concentration in each aliquot was determined by the BCA assay at 562 nm. The released fraction is the API concentration at each time point divided by the initial API concentration before dialysis (Eq. 2).

$$\text{Encapsulation efficiency} = 1 - \frac{[API]_{not\ in\ NCs}}{[API]_{total}} \quad (1)$$

$$\text{Released fraction} = \frac{[AIP]_{in\ solution}}{[API]_{initial}} \quad (2)$$

Figure 2:
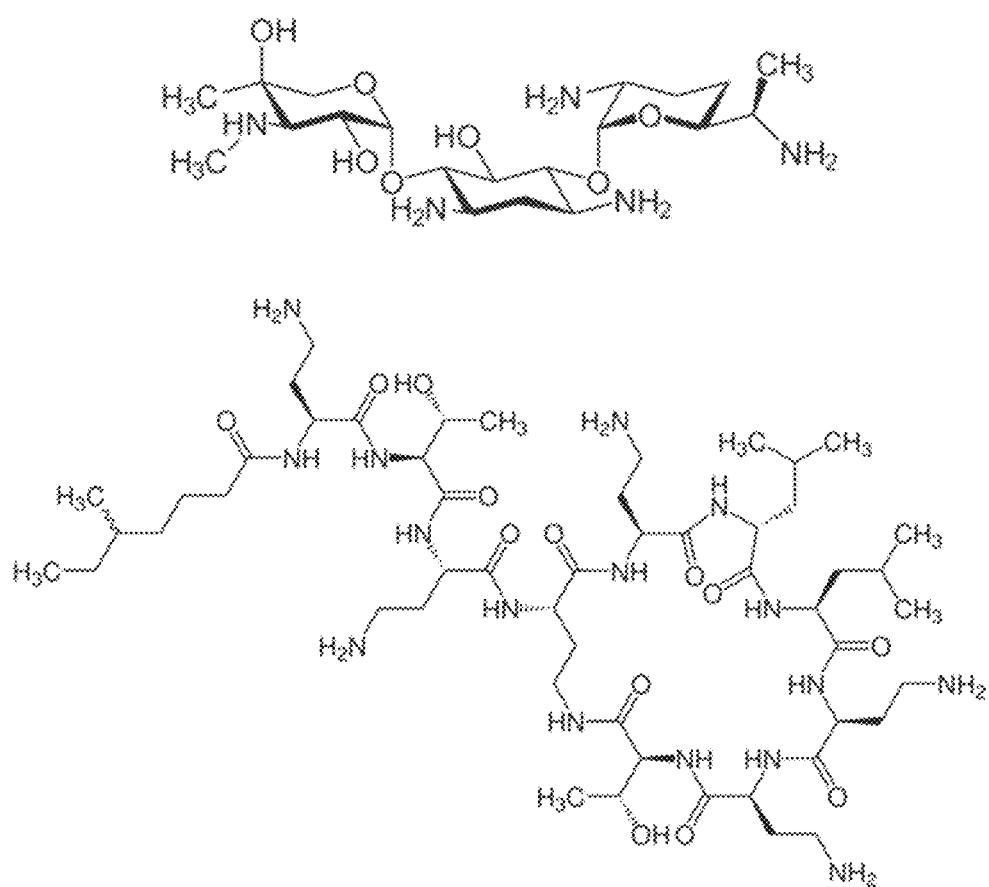
FIG. 2 shows the chemical structure of gentamicin (at top) and polymyxin B (at bottom), hydrophilic active pharmaceutical ingredients tested within the study presented herein. Gentamicin (LogP=−4.21) is an aminoglycoside having a molecular weight of 478 Da that functions by inhibiting protein synthesis. Polymyxin B (LogP=−5.62) is a macrocyclic cationic peptide having a molecular weight of 1302 Da that functions by forming pores on cell membranes. Both gentamicin and polymyxin B are active against gram-negative bacteria.

Example 1: Nanoparticles Encapsulating Gentamycin and Polymyxin B with Ion Pair Agents Hydrophobic Ion Pair Screening For successful encapsulation through nanoprecipitation methods, API:IP complexes must rapidly precipitate when mixed with an antisolvent stream (in this case an aqueous solution). However, as shown in FIG. 1, the API:IP complex may be pre-formed, and then dissolved in a water miscible organic solvent phase, or the complex may be made in situ where the hydrophobic IP is dissolved in the organic phase with the stabilizing polymer, and the water-soluble API is introduced in the aqueous phase. The APIs gentamicin and polymyxin B (FIG. 2) are highly charged hydrophilic compounds, with water solubility of >100 mg mL$^{-1}$ and >50 mg mL$^{-1}$ respectively, and with minimal solubility in polar organic solvents such as tetrahydrofuran (THF).

We first investigated preformed API:IP complexes by the following sequence of studies: (1) determination of which ion-pairs (IPs) can be used to convert the highly water soluble APIs gentamycin and polymyxin B into water-insoluble salt forms; and (2) production of salt forms that can be dissolved in highly nonpolar solvents containing THF and yield complexes that re-precipitate from THF when mixed with excess water.

Figure 3:
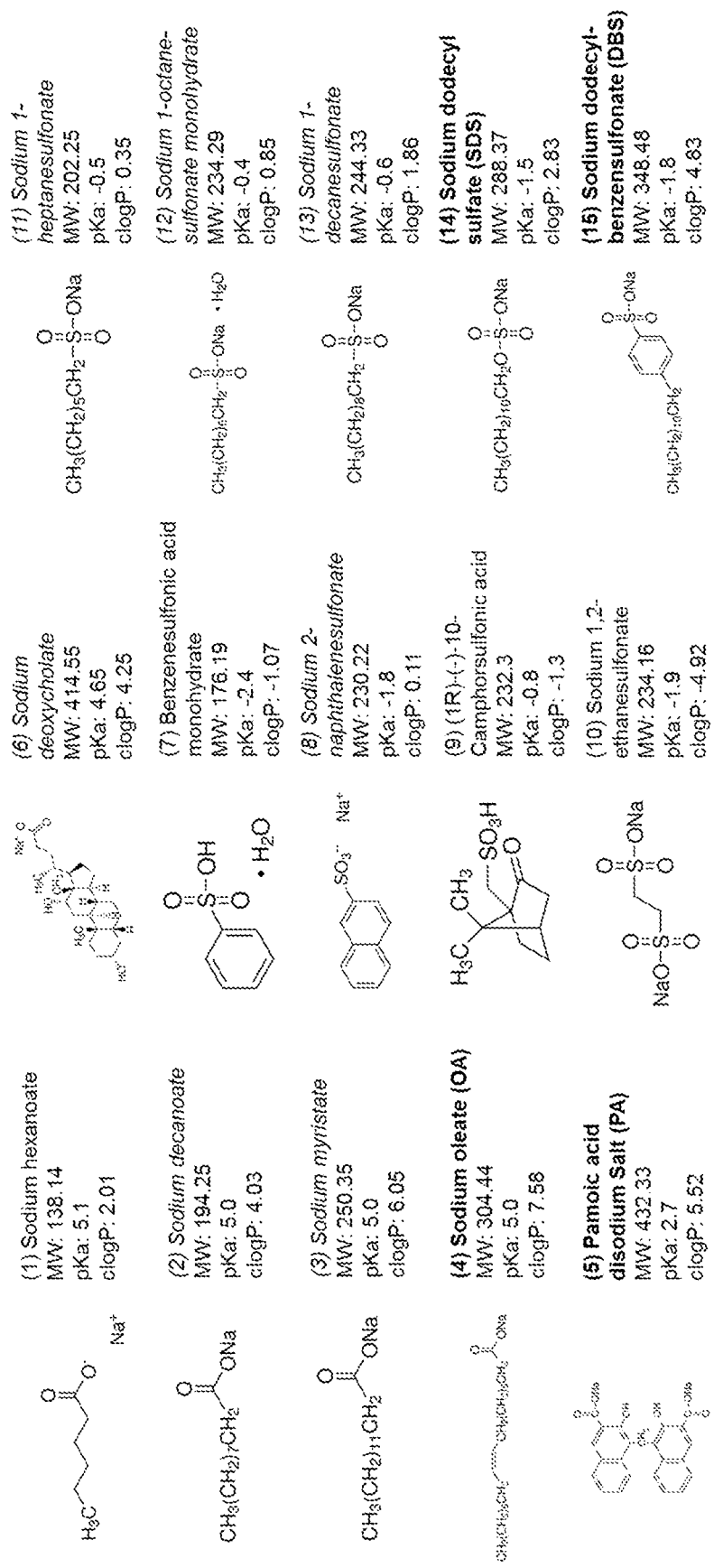
FIG. 3 shows ion pairs screened and tested within the study presented herein. A wide variety of anionic salts were used and paired against gentamicin and polymyxin B. Salts that could precipitate APIs into NCs in the FNC process are named in bold. Salts that precipitated APIs out of water, but not into NCs in the FNC process are italicized.
Figure 4:
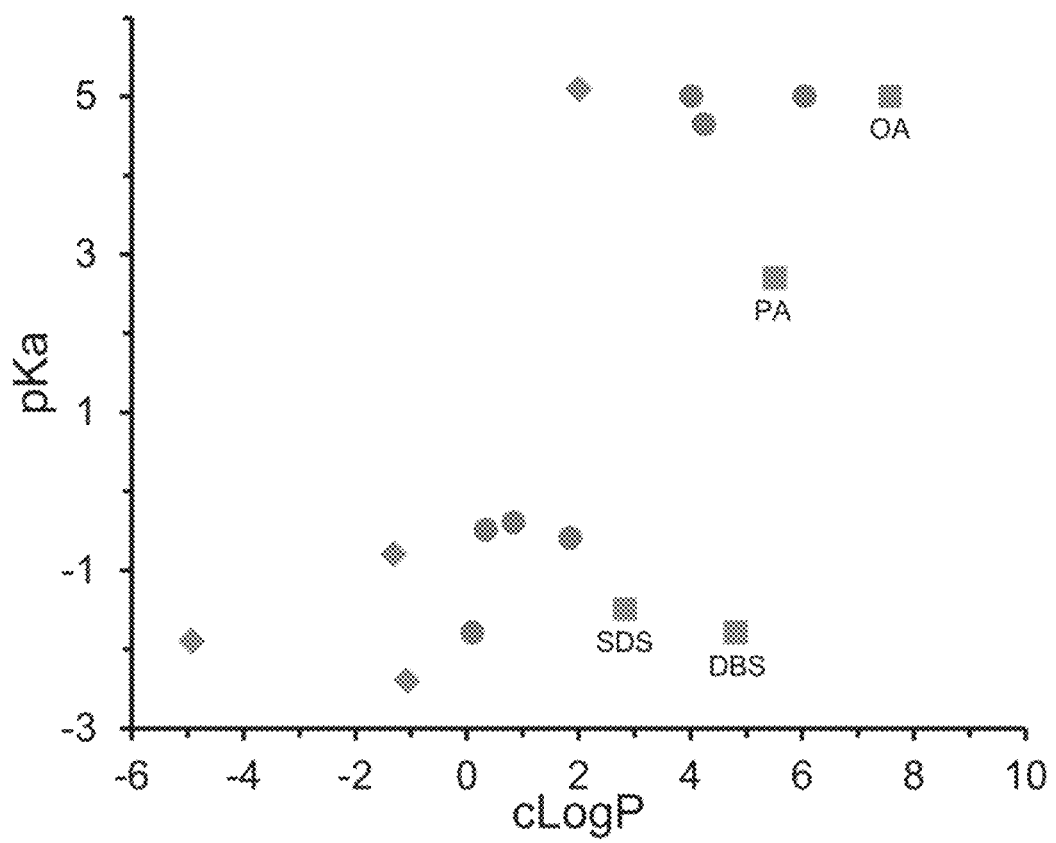
FIG. 4 provides a graph presenting the results of screening of ion pair (IP) properties for FNP-based NC assembly with polymyxin. The physical properties (pKa and cLogP) of ion pairs that failed to precipitate APIs (diamonds), that precipitated APIs but failed to produce NCs (circles), and that precipitated APIs and produced NCs (squares) are shown. The following IPs that precipitated APIs and produced NCs are labeled: sodium oleate (OA), pamoic acid disodium salt (PA), sodium dodecylbenzene sulfonate (DBS), and sodium dodecyl sulfate (SDS).

Several water-soluble counter ion salts IPs were chosen for this investigation to determine the physical properties of the counter ions required for successful complex formation (FIG. 3). A range of carboxylate and sulfonate salt IPs whose acid forms have $pK_a$ ranging 5 to −1.9 were tested, as well as salts with a wide range of solubilities and LogP values as high as 7.6 or as low as −4.92. API was dissolved at 5 mg mL$^{-1}$ in water in 1× volume, and rapidly mixed with 1× volume of dissolved IP to give a final mixture containing a 1:1 API:IP charge ratio. Mixtures were visually observed to assess if precipitates rapidly formed. Out of the fifteen IPs tested with polymyxin B, eleven IPs resulted in the formation of precipitates; four IPs did not produce an observable precipitate (FIG. 4, Tables 1 and 2). Control experiments where API or IP alone were mixed did not result in precipitation, thereby demonstrating API:IP interactions are responsible for the phase formation (phase change). As a general trend, the IPs that caused precipitation are higher MW, more hydrophobic, and of a stronger acidic form compared to IPs that did not cause precipitation. These effects can be explained by the fact that more strongly hydrophobic IPs produce more hydrophobic API:IP complexes, and that IPs that ionically interact more strongly with the APIs produce stronger API:IP complexes. In another method of quantification, IPs that caused precipitation have higher cLogP, and have acid forms with lower pKa. All IPs that caused precipitation have cLogP greater than 0.11; however one IP tested, sodium hexanoate, has a cLogP of 2.01 but did not cause precipitation. The acid form of sodium hexanoate is a weak acid with a pKa of 4.88. The comparatively poor ability of the acid form to ionize in solution limits its ability to ion pair with the API, since deprotonation of the acid is required for the required strong electrostatic interaction with the amine on the API. These results demonstrate that high IP hydrophobicity is a necessary, but not sufficient criteria of precipitating the APIs. Both hydrophobicity and strong ionic interactions are necessary.

TABLE 2

Summary of ion-pairing screening using polymyxin B API.

| Ion Pair | Precipitation | Organic Dissolution | Reprecipitation |
|---|---|---|---|
| Sodium Hexanoate | − | n/a | n/a |
| Sodium Decanoate | ++ | − | − |
| Sodium Myristate | ++ | − | n/a |
| Sodium Oleate | +++ | ++ | + |
| Pamoic Acid Disodium Salt | ++ | + | + |
| Benzenesulfonic Acid Monohydrate | − | n/a | n/a |
| Sodium 2-Naphthalenesulfonate | ++ | ++ | − |
| (1R)-(−)-10-Camphorsulfonic Acid | − | n/a | n/a |
| Sodium 1,2-Ethanedisulfonate | − | n/a | n/a |
| Sodium 1-Heptanesulfonate | + | + | − |
| Sodium 1-Octanesulfonate Monohydrate | +++ | ++ | − |
| Sodium 1-Decanesulfonate | +++ | ++ | + |
| Sodium Dodecyl Sulfate | +++ | ++ | + |
| Sodium Dodecylbenzenesulfonate | +++ | ++ | + |
| Sodium Deoxycholate | +++ | − | n/a |

In the precipitation step, + details qualitative observations of the amount of solid formed, while − details no solids formed.
In the organic dissolution test, ++ details complete dissolution, while + details non-complete dissolution.
In the re-precipitation test, + details re-precipitation observed, and − details no re-precipitation observed.

Out of the fifteen IPs tested with gentamycin, nine IPs resulted in the formation of precipitates; six IPs did not produce an observable precipitate (Tables 1 and 3).

TABLE 3

Summary of ion-pairing screening using gentamicin API.

| Ion Pair | Precipitation | Organic Dissolution | Reprecipitation |
|---|---|---|---|
| Sodium Hexanoate | − | n/a | n/a |
| Sodium Decanoate | + | − | n/a |
| Sodium Myristate | − | n/a | n/a |
| Sodium Oleate | − | n/a | n/a |
| Pamoic Acid Disodium Salt | + | + | + |
| Benzenesulfonic Acid Monohydrate | − | n/a | n/a |
| Sodium 2-Naphthalenesulfonate | ++ | ++ | − |

TABLE 3-continued

Summary of ion-pairing screening using gentamicin API.

| Ion Pair | Precipitation | Organic Dissolution | Reprecipitation |
|---|---|---|---|
| (1R)-(-)-10-Camphorsulfonic Acid | − | n/a | n/a |
| Sodium 1,2-Ethanedisulfonate | − | n/a | n/a |
| Sodium 1-Heptanesulfonate | − | n/a | n/a |
| Sodium 1-Octanesulfonate Monohydrate | ++ | ++ | − |
| Sodium 1-Decanesulfonate | +++ | ++ | + |
| Sodium Dodecyl Sulfate | +++ | ++ | + |
| Sodium Dodecylbenzenesulfonate | +++ | ++ | + |
| Sodium Deoxycholate | ++ | − | n/a |

In the precipitation step, + details qualitative observations of the amount of solid formed, while − details no solids formed.
In the organic dissolution test, ++ details complete dissolution, while + details non-complete dissolution.
In the reprecipitation test, + details reprecipitation observed, and − details no reprecipitation observed.

After successfully identifying water-insoluble API:IP complexes, it was determined whether these new salt forms could be dissolved in THF for NC processing. Pellets formed from the previous step were incubated with THF at a 1× volume equal to the starting volume of API in water. Of the eleven API:IP complexes tested, all complexes, except sodium decanoate and sodium deoxycholate, dissolved in THF. The IP sodium octanesulfonate, which has a hydrophobic eight carbon chain pendant group, was sufficient for API:IP dissolution into THF, whereas sodium decanoate, which has a hydrophobic nine carbon chain pendant group, was not. The $pK_a$ of the acid form of sodium octanesulfonate is −0.40, while that of sodium decanoate is 4.0; this effect of $pK_a$ highlights differences in the ability of these two IPs to charge interact with the APIs. Thus, although sodium decanoate is a more hydrophobic IP with a LogP of 2.01, sodium octanesulfonate with a LogP of 0.85 is a better IP agent due to its greater ability to ionically complex with APIs. As a control, APIs prepared without IP complexation were not soluble in THF, highlighting that association with hydrophobic IPs is necessary for solubility in organic solvents. These results demonstrated that IP reagents that are more hydrophobic are not necessarily better for API:IP complex formation, and IPs with lower acid form pKa can be better at forming hydrophobic salts.

In the FNP process, API:IP complexes dissolved in organic solvents must rapidly precipitate when mixed against the water antisolvent. To assess whether the nine remaining API:IP salt complexes would behave accordingly, complexes dissolved from the previous step were rapidly mixed and diluted tenfold into water.

The results of the tests are shown in FIG. 4, where the axes are the pKa of the IP agent and the calculated LogP of the compounds. Four of the IPs tested resulted in no observable precipitation upon mixing (diamonds in FIG. 4). Four of the IPs tested resulted in rapid precipitation and successful NC formation (squares); those IPs were sodium oleate (OA), pamoic acid disodium salt (PA), sodium dodecylbenzene sulfonate (DBS), and sodium dodecyl sulfate (SDS). The IPs that failed to produce precipitates at this stage were the least hydrophobic among the group, with LogP at or below 0.85, while IPs that have LogP at or above 1.86 successfully form precipitates.

Ion pairs that are the least hydrophobic and least acidic failed the first screening test, while ion pairs with intermediate hydrophobicity and acidity failed during the first and third screening tests (FIG. 4). Successful IP agents had hydrophobicities represented by logP >2.

Increasing difficulty in deprotonation, represented by increased pKa, requires greater hydrophobicity for successful NC formation. The first ionization of polymyxin occurs at pH=10.23. Therefore, the ΔpKa gap between oleic acid and polymyxin is over 5 units. In a previous study of hydrophobic APIs, ΔpKa>2 values were required for stable NC formation. For the very strongly basic polymyxin B and gentamicin, that criteria ΔpKa>2 is satisfied by all of the IP counterions. These results provided general experimental insight on candidate IP selection for hydrophobic ion pairing.

Model of IP Complex Equilibria

Without being bound by theory, in order to gain additional insight on IP selection and complexation formation procedures, a quantitative model of complexation and precipitation for basic and acidic APIs and IPs was developed and compared with experimental results. The goal was to have rules that can predict the properties of successful IP agents, and determine concentration ratios for successful FNP NC formation. For the complexation of an ionized basic API and acidic IP:

$$[API:IP] \overset{K_s}{\rightleftharpoons} [API^+] + [IP^-] \qquad (3)$$

$$\frac{[API^+][IP^-]}{[API:IP]} = K_s \qquad (4)$$

Concentrations in square brackets are given in equivalents of anionic or cationic charge, so [API⁺] indicates API in the units of molarity, with the compound having a single cationic charge. At or above saturation of ion paired complex, the concentration of aqueous API:IP is equal to the aqueous saturation concentration of API:IP.

$$[API:IP]=[API:IP]_{sat} \qquad (5)$$

Correspondingly, at or above saturation, the concentrations of aqueous API, IP, and API:IP complex are described by the equilibrium relationship of $K_s$ and that of $[API:IP]_{sat}$. While this equation is commonly reduced by combining the saturation concentrations and $K_s$ terms to provide a solubility product, it is useful to separate these terms when assessing precipitation yields.

$$\frac{[API^+][IP^-]}{[API:IP]_{sat}} = K_s \qquad (6)$$

For strongly disassociating and fully ionized API and IP, the starting concentrations of ionized compounds would be equal to the initial concentrations of the salt forms added.

$$[API^+]_0=[API]_0 \qquad (7)$$

$$[IP^-]_0=[IP]_0 \qquad (8)$$

After exceeding the solubility of the API:IP complex, precipitates form. The amount of precipitate formed is denoted as $V \times [API:IP]_{sld}$, where V is the volume of the system and $[API:IP]_{sld}$ is the concentration of API:IP complex above its saturation concentration prior to precipitation. This relationship would hold, if the volume of the precipitated solid phase is much lower than that of the initial volume of reaction such that the volume of the solution phase is essentially constant. By mass balance and combining equations (7-8), the concentration of aqueous soluble ionized API and IP are as follows:

$$[API^+]=[API^+]_0-[API:IP]_{sat}-[API:IP]_{sld} \quad (9)$$

$$[IP^-]=[IP^-]_0-[API:IP]_{sat}-[API:IP]_{sld} \quad (10)$$

Substitution of (9-10) into (6), yields a general expression that relates the starting concentrations of aqueous API and IP with the moles of solid precipitated API:IP complex.

$$\frac{([API]_0 - [API:IP]_{sat} - [API:IP]_{sld})([IP]_0 - [API:IP]_{sat} - [API:IP]_{sld})}{[API:IP]_{sat}} = K_s \quad (11)$$

Solving for the precipitated API:IP complex, the expression for the solid precipitate is obtained.

$$[API:IP]_{sld} = \frac{1}{2}\Big([API]_0 + [IP]_0 - 2[API:IP]_{sat} - \sqrt{[API]_0^2 + [IP]_0^2 - 2([API]_0[IP]_0) + 4K_s[API:IP]_{sat}}\Big) \quad (12)$$

This expression holds for concentrations above the API:IP saturation concentrations. For the complexation of the strongly basic polymyxin B and gentamicin at neutral pH ~7, and at concentrations where precipitates had formed, these conditions are satisfied. Thus, under these assumptions and conditions, the bulk concentration of precipitated API:IP is a function of the starting concentrations of API and IP, the equilibrium constant $K_s$, and aqueous saturation solubility $[API:IP]_{sat}$—all of which are readily determined. Whereas the $K_s[API:IP]_{sat}$ term is typically simplified to a $K_{sp}$ solubility product, separation of these two terms provides mechanistic insight on precipitation yields. $K_{sp}$ is a function of complexation strength and molecular actions between the API and IP (the charged groups between the API and IP), while the $[API:IP]_{sat}$ is a function of the hydrophobicity of the IP complex, e.g., a function of the complex hydrophobicity and interactions with water due to the hydrophobic tail group on the IP.

Figure 5A:
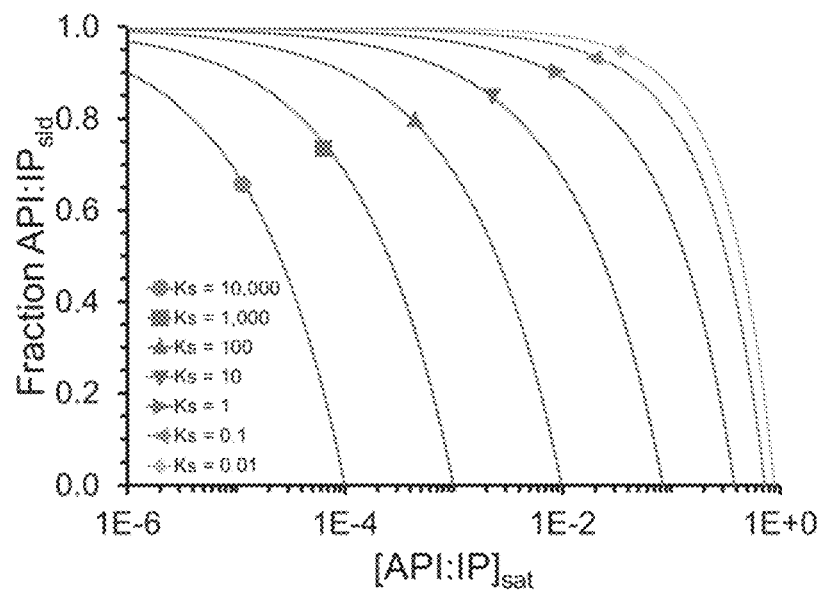
FIG. 5A provides a graph illustrating the modeling of API precipitation conditions by utilizing equation (10). The fraction of API that is precipitated with varying saturation solubilities of the API:IP complex and with varying tendencies of complex formation (complexation strength) is shown. Saturation solubility is noted with $[API:IP]_{sat}$ and has units of mol $L^{-1}$. Complexation strength is noted with $K_s$ and has dimensions of $mol^{-1} L^{-1}$. The amounts of API and IP included in the reaction are at a one-to-one ratio at 1 M.
Figure 5B:
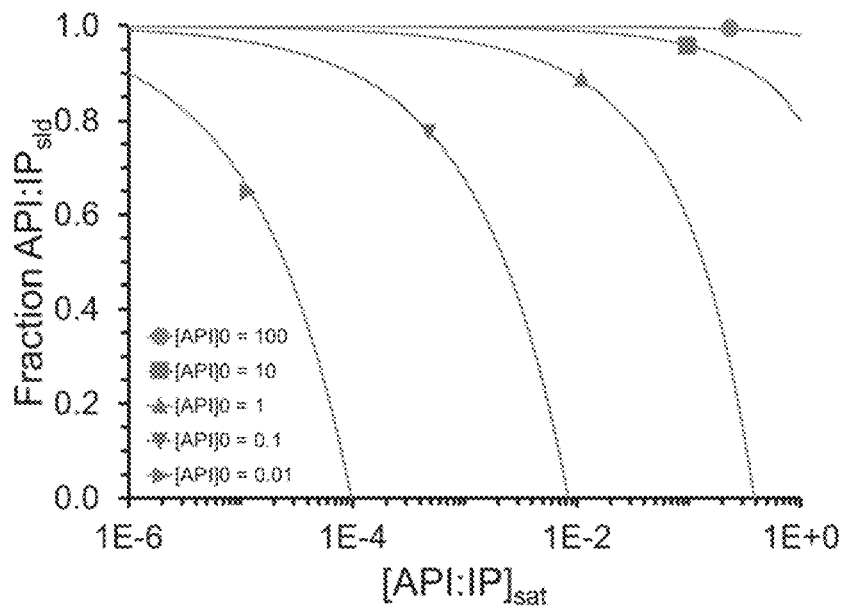
FIG. 5B provides a graph illustrating the modeling of API precipitation conditions by utilizing equation (10). The fraction of API that is precipitated with varying saturation solubilities of the API:IP complex, and by varying the amount of API in the reaction. The amounts of API and IP included in the reaction are at a one to one ratio. $[API]_0$ has dimensions of M. Precipitation yields can be increased by decreasing complex saturation solubility, by increasing complexation strength, or by increasing the concentration of the reaction.

Inspection of Eq. 12 provides insight on how to design precipitation reactions for NC processing, as shown in FIGS. 5A and 5B. For a system with $K_s$ and initial API and IP concentrations, the fraction of initial API that precipitates increases as the $[API:IP]_{sat}$ values decrease, as shown in FIG. 5A. The following conditions were used to generate FIG. 5A: $[API]_0=1$ M; $[IP]_0=1$ M; $10^{-6}$ M$<[API:IP]_{sat}<1$ M; and $10^{-2}$ M$^{-1}<K_s<10^4$ M$^{-1}$. If the complex is below a critical $[API:IP]_{sat}$ value, no solids are formed. Highly hydrophobic IPs result in the formation of API:IP complexes with lower saturation solubilities—which is in agreement with our experiment results that higher LogP complexes are better precipitate formers. For a system with a defined $[API:IP]_{sat}$, and constant starting API and IP initial concentrations, the fraction of initial API that precipitates increases as the $K_s$ of the complex decreases (FIG. 5A). If the complex exhibits $K_s$ above a critical value, no solids are formed. These results highlight that IPs with strong counter ion interactions with the API maximize complex formation-which is reflected in the experimental results observed, where IPs with lower acid form $pK_a$ are more effective in forming precipitates, even if the IP itself is less hydrophobic.

For a system with a specific $[API:IP]_{sat}$ and $K_s$, the fraction of initial API that precipitates increases as the initial concentrations of API and IP increase, as shown in FIG. 5B. The following conditions were used to generate FIG. 5B: $10^{-2}$ M$<[API]_0<10^2$ M; $[API]_0=[IP]_0$; $10^{-6}$ M$<[API:IP]_{sat}<1$ M; and $K_s=1$ M$^{-1}$. Below a critical starting API and IP initial concentrations, no precipitates are formed. The complex can be driven to nearly complete complexation of API by increasing the IP concentration, which corresponds to Le Chatlier's principle. However, this only occurs if individually the species are soluble. If one species precipitates or micellizes, then adding more of that species does not further drive the reaction. In that case the individual ion concentrations in Eq. 3 would be given by the solubility product of the insoluble solid phase or by the CMC of the micellizing species. In that case an additional set of solubility products and mass balances would have to be added to the balances given by Eqns. 3-12. If there are two solid phases that can be formed, that is, an insoluble ion pair complex (API:IP) and a solid phase of the IP, then NCs can be formed, but the stoichiometry of the core of the NC will not be determined by the stoichiometry of the ion pair, but by the molar ratio of complex and insoluble IP. These results provide a model to guide IP choice and precipitation reaction conditions for NC processing, and the model supports the experimental results observed.

Flash NanoPrecipitation of API:IP Complexes

Figure 6A:
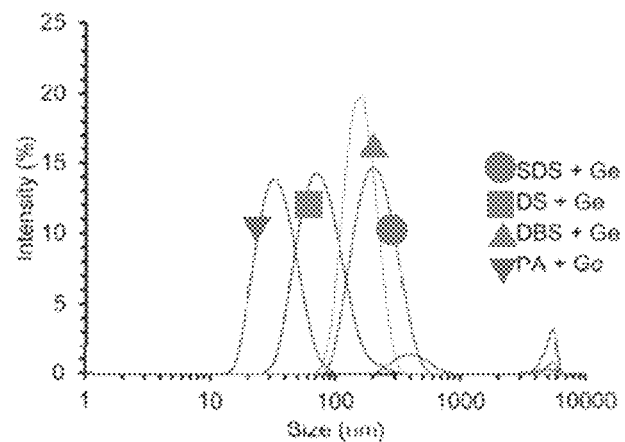
FIG. 6A provides a graph of size distributions of NPs formed using gentamycin as a pre-formed API:IP complex using the IPs sodium dodecyl sulfate (SDS), decyl sulfate (DS), sodium dodecylbenzene sulfonate (DBS), and pamoic acid disodium salt (PA). Compositions of NC formulations are given in Table 1.
Figure 6B:
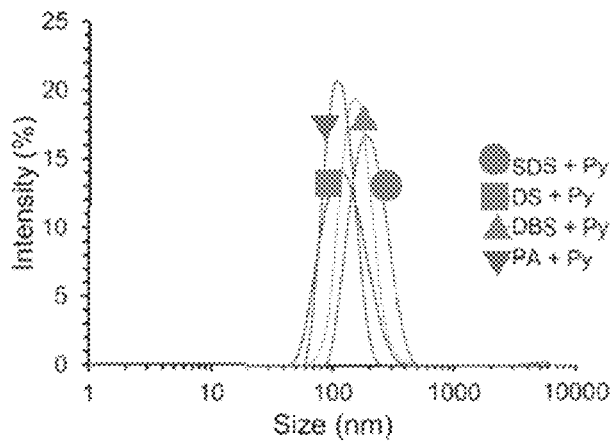
FIG. 6B provides a graph of size distributions of NPs formed using polymyxin B as a pre-formed API:IP complex using the IPs sodium dodecyl sulfate (SDS), decyl sulfate (DS), sodium dodecylbenzene sulfonate (DBS), and pamoic acid disodium salt (PA). Compositions of NC formulations are given in Table 1.
Figure 6C:
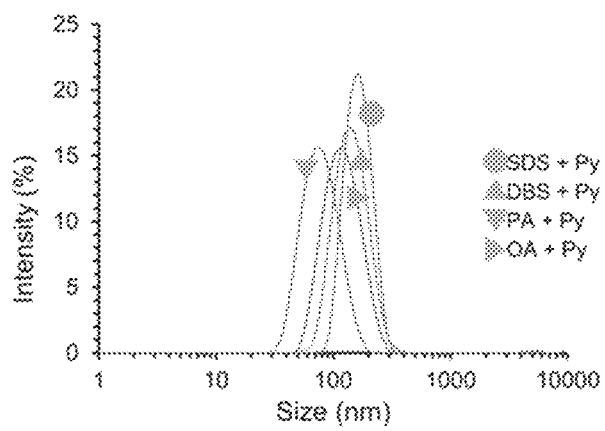
FIG. 6C provides a graph of size distributions of NPs formed with in situ ion pairing of polymyxin B using the IPs sodium dodecyl sulfate (SDS), sodium dodecylbenzene sulfonate (DBS), pamoic acid disodium salt (PA), and sodium oleate (OA). Compositions of NC formulations are given in Table 1.

The four IP candidates (OA, SDS, DBS, PA) that passed the screening process were used to form NCs with the FNP process. Gentamicin and polymyxin B were precipitated with IPs and dissolved into THE as described above, and mixed with PCL-PEG dissolved in THF to yield an organic THE stream containing both polymeric stabilizer and API:IP complex. This stream was rapidly mixed against water within a confined impingement jet to precipitate API:IP complex in the presence of the amphiphilic PCL-PEG to form NCs. DLS analysis of the resultant samples demonstrated that NCs 50-200 nm with narrow polydispersity were formed (FIGS. 6A and 6B, Table 1).

No particles, only PCL-PEG micelles, were formed when only stabilizer and API, or when only stabilizer and IP, was used in the FNC process, with the exception of OA (Table 1). Large aggregates were formed when only API and IP was included during the FNC process, demonstrating that the inclusion of all three stabilizer, API, and IP components are simultaneously needed for NC formation. These results demonstrate that while water-soluble APIs cannot be formulated into NCs, hydrophobic API:IP complexes can be formed into NCs with the water-precipitation process.

NC formation using pre-formed API:IP complex is, therefore, demonstrated. However, there are advantages to in situ API:IP NC complex formation, since NC formation could be accomplished in a single step. This single step would simplify processing. That is, although APIs can be preformed into hydrophobic API:IP complexes using batch processes prior to FNP, a single continuous processing step that can result in both API complexation and NP formation can simplify production procedures and reduce production costs. To test in situ complexation and NC formation and assess if APIs can be encapsulated in a single continuous step by in situ complexation, polymyxin B dissolved in water was impinged against organic solvent containing IP and PCL-PEG in the FNP process. The IPs previously identified as capable of forming NCs using pre-formed complexes were studied using this method. Out of the IPs assessed, all converted polymyxin B into hydrophobic forms in situ during mixing to yield stable NCs with narrow size distributions (FIG. 6C). By comparing FIGS. 6B and 6C, where FIG. 6B is for the pre-formed IP, and FIG. 6C is the in situ ion paired polymyxin, one sees that the NC sizes produced by either process are essentially equivalent. Control experiments, in which PCL-PEG and IP only, or PCL-PEG and polymyxin B only were used resulted in empty micelles and not in NC formation. Control experiments where IP and polymyxin B only were used resulted in the formation of aggregations, together demonstrating that all three components—stabilizer, API, and IP—are required for in situ complexation and NC formation.

To measure the encapsulation efficiency of polymyxin B, free un-encapsulated drug was separated from that which was encapsulated in NCs through ultrafiltration across a 100 kDa membrane, and characterized with BCA analysis. The encapsulation efficiency is based on the relative ratio of free drug compared to the total amount of drug included in the FNC system.

$$\text{Encapsulation Efficiency} = 1 - \frac{[\text{Polymyxin B}]_{free}}{[\text{Polymyxin B}]_{total}}$$

At a 1:1 IP to API charge ratio, polymyxin B was encapsulated with efficiency greater than 95% efficiency for all IPs tested. At excess IP, high encapsulation efficiency was retained, but at a 0.5:1 IP to API charge ratio, encapsulation efficiency dropped significantly, to ~70% in the case of sodium oleate. These results demonstrate that decreasing the amounts of IP relative to API that is present can cause decreased encapsulation efficiencies, by increasing the relative amount of solubilized API that is not retained in the core by ion pairing.

NC Stability

NC stability was assessed by measuring the size distributions of the NCs when diluted into a closed volume of water or PBS, all at room temperature. Although characterization of NPs in a closed volume does not capture the sink conditions that would be present in vivo, behavior in closed systems can shed insight on NP properties. When paired with at least one charge equivalent of counterion for the four counterions tested, nanoparticle size remained mostly constant in water, despite minor ripening or swelling. When diluted tenfold into PBS, however, particles exhibited size changes over time, which are driven by ion exchange between the anionic IP and the $Cl^-$ and $PO_4^{-3}$ ions in PBS. The ion exchange releases the bound API, which is soluble in the external phase. In the case of pamoic acid IPs, particles shrank in size, which suggests simple dissolution of encapsulated API from the NC core (Table 4A). (Polydispersity index at the several times is shown in Table 4B.) In the case of sodium dodecylbenzenesulfonate (DBS), sodium dodecyl sulfate (SDS), and sodium oleate (OA), particles increased in size over time. These results are consistent with Ostwald ripening of particles, where complexes and API are released into solution but subsequently redeposit onto particles of larger size, resulting in particle size growth over time [Liu Y, Kathan K, Saad W, Prud'homme R K. Ostwald ripening of beta-carotene nanoparticles. *Phys Rev Lett*. 2007 Jan. 19; 98 (3): 036102.]. The least hydrophobic of these IPs, sodium dodecyl sulfate (SDS), demonstrated the greatest size change rates over time, while those IPs with greater hydrophobicity and lower $pK_{a\ exhibited}$ size changes at a slower and smaller (lesser) extent. Increasing the IP ratio above 1:1 increased stability. For IP ratios above 1:4 resulted in NCs that did not change size, even in PBS, over 72 hours. This is consistent with the model, which would show that increasing IP, would drive higher complexation. These results demonstrate that while NP are stable over time in solution and for storage in deionized water, transfer into high ionic strength PBS can initiate changes in NP structure, to an extent that is dependent on the structure of the IP that is initially used.

TABLE 4A

Stability of NCs when diluted into PBS over time. The ion pairs (IPs) used to form the NCs through FNP processing were sodium dodecylbenezenesulfonate (DBS), pamoic acid disodium salt (PA), sodium oleate (OA), and sodium dodecyl sulfate (SDS). Size data are not shown for particles that had increased beyond the effective measurement range of the DLS by 48-72 h.

|         | T = 0   | T = 3 h   | T = 24 h  | T = 72 h |
|---------|---------|-----------|-----------|----------|
| 1:1 DBS | ~150 nm | ~200 nm   | ~200 nm   | ~200 nm  |
| 1:1 PA  | ~75 nm  | ~75 nm    | ~75 nm    | ~75 nm   |
| 1:0.5 OA| ~200 nm | >1000 nm  | >1000 nm  |          |
| 1:1 OA  | ~200 nm | ~400 nm   | ~500 nm   |          |
| 1:2 OA  | ~150 nm | ~200 nm   | ~300 nm   | ~400 nm  |
| 1:4 OA  | ~150 nm | ~150 nm   | ~150 nm   | ~150 nm  |
| 1:0.5 SDS| ~175 nm| ~500 nm   | ~500 nm   |          |
| 1:1 SDS | ~175 nm | ~500 nm   | >1000 nm  |          |
| 1:2 SDS | ~175 nm | ~225 nm   | ~250 nm   | ~350 nm  |
| 1:4 SDS | ~175 nm | ~175 nm   | ~175 nm   | ~175 nm  |

TABLE 4B

PDI of NCs when diluted into PBS over time. The ion pairs (IPs) used to form the NCs through FNP processing were sodium dodecylbenezenesulfonate (DBS), pamoic acid disodium salt (PA), sodium oleate (OA), and sodium dodecyl sulfate (SDS).

|         | T = 0  | T = 3 h | T = 24 h | T = 72 h |
|---------|--------|---------|----------|----------|
| 1:1 DBS | ~0.15  | ~0.15   | ~0.3     | ~0.3     |
| 1:1 PA  | ~0.25  | ~0.25   | ~0.25    | ~0.25    |
| 1:0.5 OA| ~0.1   | ~0.3    | ~0.3     |          |
| 1:1 OA  | ~0.1   | ~0.2    | ~0.3     |          |
| 1:2 OA  | ~0.05  | ~0.1    | ~0.1     | ~0.1     |
| 1:4 OA  | ~0.1   | ~0.1    | ~0.1     | ~0.1     |
| 1:0.5 SDS| ~0.25 | ~0.7    | ~0.7     |          |
| 1:1 SDS | ~0.2   | ~0.25   | ~0.6     |          |
| 1:2 SDS | ~0.05  | ~0.05   | ~0.2     | ~0.3     |
| 1:4 SDS | ~0.1   | ~0.05   | ~0.05    | ~0.05    |

Because encapsulation efficiency was a function of the amount of IP that was included during NP processing, we sought to also investigate how particle size stability was affected by the amount of IP included in NP processing. NPs were made with IP to API charge ratios between 0.5 to 4, using sodium dodecyl sulfate (SDS) and sodium oleate (OA) as IPs. These NPs exhibited a wide range of stability profiles when diluted into a closed volume of PBS, ranging from rapid ripening under three hours, to small size changes over days, or no size changes over days. As an important note, size changes are exhibited as a shift of mean-peak diameters, as would occur in the case of Ostwald ripening, and are not the formation of aggregates, which would occur if there were API release and precipitation/recrystallization. Aggregation would be seen as a significant increase in the polydispersity, PDI. NP stability increased as the amount of IP included in the system increased; this result is consistent with the phenomenon that by increasing the concentration of IP during NP processing, at a constant API concentration, the formation of the API:IP complex is further favored. This is especially relevant in the case of polymyxin B, as there are multiple sites for ion-pairing on the API. While outside the scope of this current proof of concept experiment, interesting future work includes determining the exact solid-state compositions of the materials formed to provide insight on the behavior of these NPs. Together, these results highlight that the ratio of IP to API during NP processing is an additional handle to tune NP properties and stability.

API Release from NCs

Figure 7A:
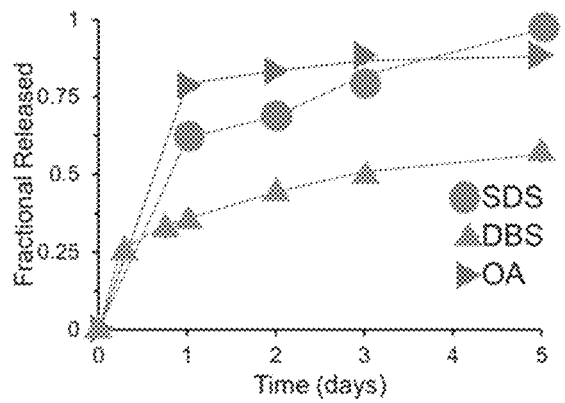
FIG. 7A provides a graph showing release rates (fraction released as a function of time) of polymyxin B NCs when using 1:1 API to IP charge ratio for the IPs sodium dodecyl sulfate (SDS), sodium dodecylbenzene sulfonate (DBS), and sodium oleate (OA).
Figure 7B:
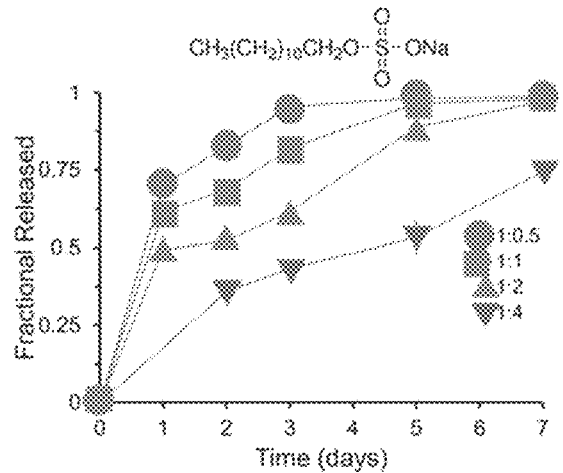
FIG. 7B provides a graph showing release rates (fraction released as a function of time) of polymyxin B NCs when using sodium dodecyl sulfate (SDS) IP for several API:IP ratios. The charge ratio is given as 1:x, where x is the number of ion pair (IP) charge equivalents of the positively-charged API.
Figure 7C:
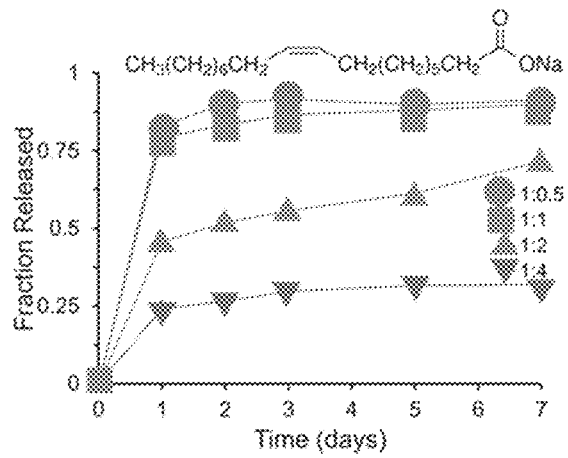
FIG. 7C provides a graph showing release rates (fraction released as a function of time) of polymyxin B NCs when using sodium oleate (OA) IP for several API:IP ratios. The charge ratio is given as 1:x, where x is the number of ion pair (IP) charge equivalents of the positively-charged API.

API release rates from NCs are a critical determinant of dosing frequency, in vivo active concentrations, and overall therapeutic effectiveness. The release rates of polymyxin B were assessed by enclosing NCs in an 8 kDa MWCO dialysis bag and diluting into a thousand-fold excess volume of PBS to simulate an "open sink" condition at room temperature. Encapsulated polymyxin within dialysis bags was measured over time, using the BCA assay, to determine the amount of API that had been released (FIGS. 7A, 7B, and 7C). FIGS. 7A, 7B, and 7C show the release results for the three anionic groups studied, SDS, DBS, and OA, and they show API:IP ratios for SDS and OA of from 1:0.5 to 1:4.

At a constant 1:1 IP to API charge ratio, the release rate profiles of NPs (NCs) varied depending on the identifies of the IP used. The IPs with a more hydrophobic pendant side chain, and charge group with a lower acid form pKa resulted in the formation of particles with slower release rates. NPs made with sodium decanesulfonate and sodium oleate release rapidly, with near complete dissolution within one day. This result is consistent with visual observations of the NP constructs, which were initially opalescent but which appeared clear after one day of dialysis. In the case of sodium dodecyl sulfate and sodium dodecylbenzenesulfonate, NPs remained visually opalescent over time even to up to five days of dialysis. This corresponded with slower release rates and higher concentrations of retained polymyxin B over time as determined by BCA analysis. NPs made with To assess if the ratio of IP: API during NP formation affected release profiles, NPs were made using 1:0.5, 1:1, and 1:4 IP to API ratios (see FIGS. 7B and 7C). By increasing the amount of IP that is present during NP formation, the release rate of polymyxin B was decreased, in both the case of sodium dodecyl sulfate and sodium oleate. This demonstrates that NP release rates can be tuned not only by varying the IP identity as seen above, but also by varying the IP: API precipitation conditions. Increasing the amount of IP added during FNP increases NP size.

The stability with SDS is interesting, given the high solubility of SDS in solution: SDS is soluble in aqueous solution up to 8 mM prior to micellization. In a study with small molecule APIs with single ionic sites, the ion pairing was shown to be 1:1. Polymyxin B has four secondary amines and 11 amide nitrogens. Without being bound by theory, the interactions with SDS may involve non-stoichiometric association. This SDS interaction may be similar to the SDS: protein interactions which are the basis for SDS electrophoresis. The denatured protein backbone would be similar to the peptide backbone in polymyxin B. The SDS binding to proteins is cooperative and results from both ionic interactions and cooperative alkyl chain interactions among the SDS molecules associated with the backbone, as has been elucidated in the paper by Turro et al. [Turro, N.J., et al., Spectroscopic probe analysis of protein-surfactant interactions: the BSA/SDS system. *Langmuir*, 1995. 11 (7): p. 2525-2533.]. The combination of ionic interactions and surfactant tail association can lead to intricate structures which have been demonstrated for ionic polymers and DNA by x-ray diffraction [Antonietti, M., J. Conrad, and A. Thuenemann, Polyelectrolyte-Surfactant Complexes: A New Type of Solid, Mesomorphous Material. *Macromolecules*, 1994. 27 (21): p. 6007-6011.]. These more complex structures are not strictly stoichiometric, but are determined by geometrical arrangement. The peptide ion paired complexes discussed herein may display similar structural features.

Very hydrophobic lipids and alkyl acids and unsaturated acids are those with logP values greater than 3 at pH=7. Also, very hydrophobic cationic counterions can be used, which have the same values of LogP. LogP values can be calculated using Mol Inspiration software. With very hydrophobic counterions the release of soluble actives from the surface layer can lead to an encapsulation of interior actives. This encapsulation is demonstrated in FIG. 7C for oleic acid, which at ratios of active to oleic acid of 1:2 or 1:4 leads to a plateau in the released amount.

Example 2: Nanoparticles Encapsulating Mastoparan 7 and Mastoparan 17 with Ion Pair Agents Mastoparan 7 (MP7) is a cationic antibiotic peptide having a molecular weight of 1422 Da with sequence INLKALAALAKALL-NH$_2$ [SEQ ID NO: 1] (conventional single-letter amino acid abbreviation used). 11 (79%) of its 14 amino acids are hydrophobic (nonpolar), and 2 (14%) of its 14 amino acids are basic. It has a +3 charge. Mastoparan 17 is a non-active derivative of MP7 that is used as a control for activity tests.

MP7 was ion paired and encapsulated using the ion pairing and Flash NanoPrecipitation approach. Its release from nanoparticles was measured, and was found to depend on the counterion used. This finding is consistent with the results from the polymyxin B experiments. Nanoparticles containing encapsulated MP7 were then tested in vivo to demonstrate that the drug retained its activity throughout the steps of ion pairing, encapsulation, and release.

MP7 was encapsulated into nanoparticles using ion pairing and Flash NanoPrecipitation. First, MP7 (5 mg/ml) was ion paired with sodium dodecyl sulfate (SDS) at a 1:1 charge ratio in water. A precipitate was observed, indicating the formation of an insoluble ion paired complex. The complex was frozen and dried by lyophilization, then resuspended in a mixture of tetrahydrofuran (THF) and dimethylsulfoxide (DMSO) as a solution, and that solution then loaded into an organic (THF) feed stream containing a polycaprolactone (5 kDa)-block-polyethylene glycol (5 kDa) (PCL$_{5k}$-b-PEG$_{5k}$) block copolymer. That organic feed stream was impinged against water in a confined impinging jet (CIJ) mixer. NPs ~120 nm in diameter and with PDI <0.2 were formed through this Flash NanoPrecipitation (FNP) technique.

Encapsulation efficiency and MP7 release were measured as described above. Encapsulation efficiency was measured to be over 95%. Release from free MP7 and MP7 in NPs was measured. The characteristic release time (time for 50% release) of encapsulated MP7 from NPs was 30 hours, which was significantly longer than the 2.9 hour characteristic release time from unencapsulated MP7. Thus, encapsulation within NPs resulted in extended release. This NP formulation released all its MP7 by 7 days.

Figure 8:
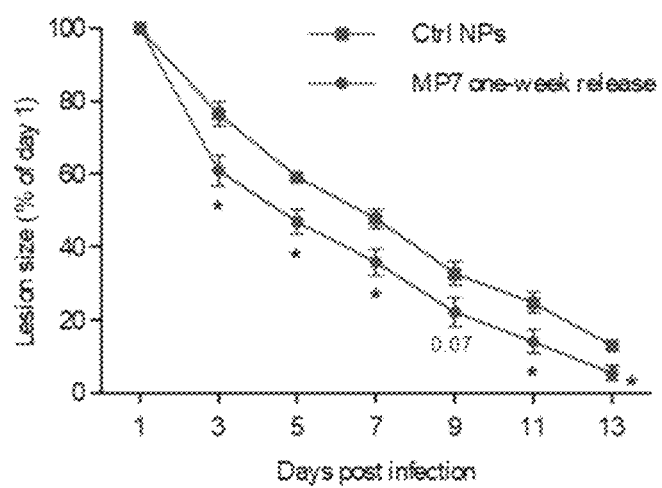
FIG. 8 provides a graph showing decrease in the size over time of an s. *aureus* infected lesion on a mouse's back upon injection with control NPs without MP7 and upon injection with NPs containing NP7.

This 'one-week release' formulation was tested in vivo in a dermonecrotic s. *aureus* wound model. In brief, a wound was made on a mouse's back, then infected with s. *aureus*. A one-time injection of NPs with or without MP7 was injected into the wound, and lesion size was measured over time. The results shown in FIG. 8 demonstrate that the delayed-release formulation improved wound healing (experiments performed by M. Arifuzzaman).

Release was further extended by the addition of sodium oleate (OA) into the formulation. When sodium oleate was added in addition to SDS, complete release was slowed to two weeks. This finding is consistent with the polymyxin B result that oleate-containing ion paired formulations release more slowly than SDS-containing formulations.

MP17 is an inactive version of MP7 that will be used as a control in a repeat of the experiment above. MP17 was successfully ion paired with the same counterion (SDS) as MP7 and encapsulated into NPs. A hydrophobic dye, ETTP5, was co-encapsulated with MP17, demonstrating the compatibility of the ion pairing approach with traditional FNP. By pairing ion pairing FNP with regular FNP, co-encapsulation of hydrophilic and hydrophobic materials is possible.

Example 3: Nanoparticles Encapsulating Sub5 with an Ion Pair Agent

Sub5 is a cationic antibiotic peptide with the sequence RRWKIVVIRWRR-NH$_2$ [SEQ ID NO: 2]. It contains 12 amino acid residues and has a molecular weight of 1723 Da (Daltons, g/mol). 6 (50%) of its 12 amino acids are hydrophobic (nonpolar), and 6 (50%) of its 12 amino acids are basic. It has a +7 charge. Sub5 was ion paired and encapsulated using the ion pairing and Flash NanoPrecipitation approach. Its release from nanoparticles was measured, and was found to be different from MP7's even under the same ion pairing conditions. This demonstrated that the release of an ion paired hydrophilic active depends on (1) the counterion used, (2) the charge ratio of active to counterion, and (3) the active itself.

Sub5 was encapsulated into nanoparticles using ion pairing and Flash NanoPrecipitation. First, Sub5 (5 mg/ml) was ion paired with sodium dodecyl sulfate (SDS) at a 1:1 charge ratio in water. A precipitate was observed, indicating the formation of an insoluble ion paired complex. The complex was frozen and dried by lyophilization and then resuspended in a mixture of THF and DMSO as a solution, and that solution was then loaded into an organic (THF) feed stream containing $PCL_{5k}$-b-$PEG_{5k}$ block copolymer. That organic feed stream was impinged against water in a confined impinging jet (CIJ) mixer. NPs ~120 nm in diameter and with PDI <0.2 were formed through this FNP technique.

Encapsulation efficiency and Sub5 release were measured as described above. Encapsulation efficiency was measured to be over 95%. Release from free Sub5 and Sub5 in NPs was measured. The characteristic release time (time for 50% release) of Sub5 from NPs was 6.9 days, which was significantly longer than the 2.1 hour characteristic release time from unencapsulated Sub5. Thus, encapsulation within NPs resulted in extended release.

Example 4: Nanoparticles Encapsulating LL37 with Ion Pair Agents

LL37 is a cationic antibiotic peptide with sequence FKRIVQRIKDFLR [SEQ ID NO: 3]. It contains 13 amino acid residues and has a molecular weight of 1719 Da. 6 (46%) of its 13 amino acids are hydrophobic. It has a +4 charge. LL37 was ion paired and encapsulated using the ion pairing and Flash NanoPrecipitation approach.

LL37 was ion paired with sodium dodecyl sulfate (SDS) at a 1:1 charge ratio in water; the resulting complex was dried by lyophilization and then resuspended in a mixture of THF and DMSO. This organic solution was mixed with a THF solution containing PCL5k-b-PEG5k block copolymer to create the organic feed stream for FNP. That stream was impinged against water to form NPs ~120 nm in diameter. Encapsulation efficiency was measured as described above to be over 95%.

Example 5: Nanoparticles Encapsulating Colistin with an Ion Pair Agent

Figure 9:
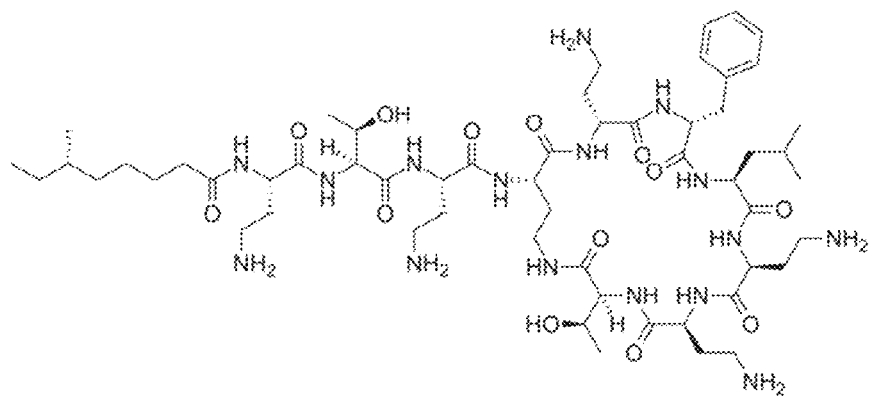
FIG. 9 shows a comparison of the chemical structures of polymyxin B sulfate and colistin ("polymyxin E").
Figure 9:
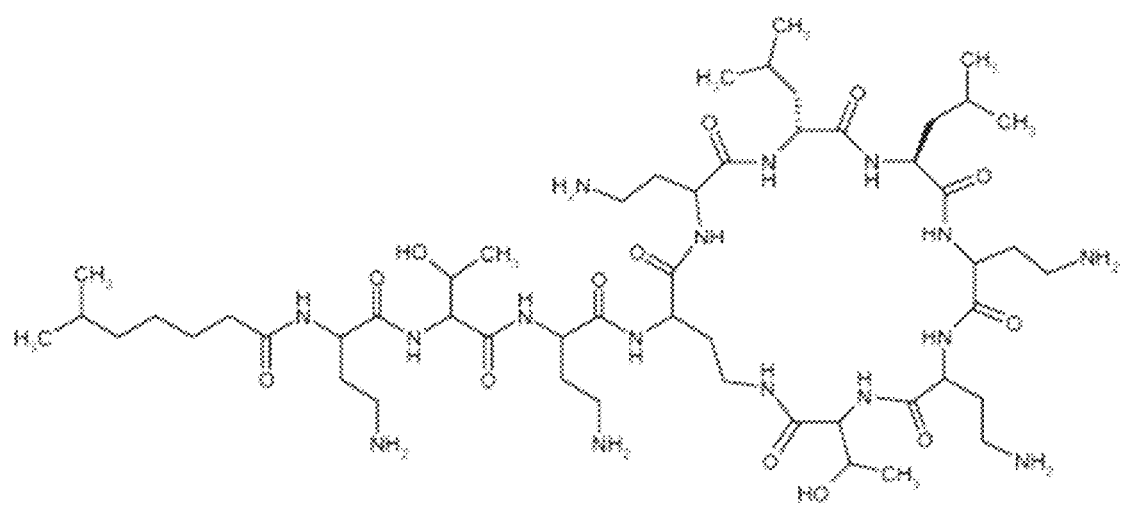

Colistin ("polymyxin E") is a cyclic peptide having a molecular weight of 1155 Da. A structural comparison of colistin with polymyxin B sulfate is shown in FIG. 9. A difference is that polymyxin B has an aromatic ring but colistin does not.

Figure 10:
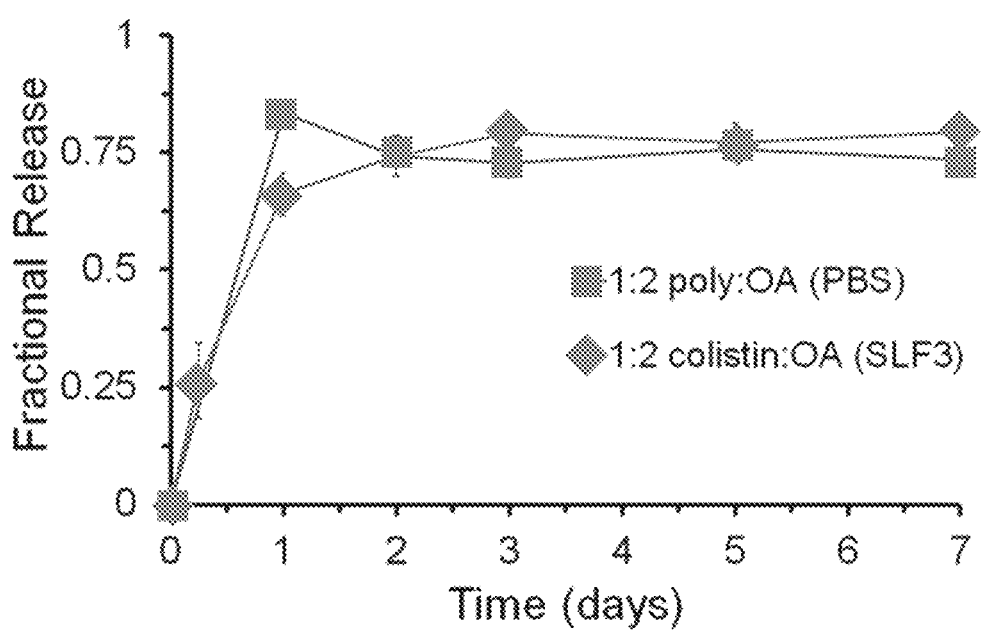
FIG. 10 provides a graph showing release rates (fraction released as a function of time) of polymyxin B (poly) from NCs formed using sodium oleate (OA) IP in phosphate buffered saline (PBS) and of colistin from NCs formed using sodium oleate (OA) IP in simulated lung fluid (SLF3).

Colistin was ion paired in situ with sodium oleate (OA) and encapsulated. Colistin was dissolved at 5 mg/mL in water. This stream was impinged against an organic stream of 50/50 v/v % tetrahydrofuran (THF) and methanol (MeOH). This organic solution contained PCL5k-b-PEG5k block copolymer and sodium oleate. NPs ~100 nm in diameter were formed. Colistin release from these NPs was measured and compared to polymyxin B release. The release of colistin was similar to that of polymyxin B (see FIG. 10).

Example 6: Nanoparticles Encapsulating Ecumicin with an Ion Pair Agent

Ecumicin is a cationic cyclic peptide having a molecular weight of 1599 Da with 1 secondary amine and 1 tertiary amine. It has a +2 charge. It is active against *M. tuberculosis* in vivo. Ecumicin was ion paired and encapsulated using the ion pairing and Flash NanoPrecipitation approach. Vitamin E succinate was used as the counterion (ion pair agent).

Ecumicin was encapsulated within PCL-b-PEG nanoparticles by the ion pairing Flash NanoPrecipitation approach. Ecumicin was loaded in an organic stream of 50/50 v/v % THF and MeOH along with PCL-b-PEG and vitamin E succinate (vitE succinate) and impinged against a water stream in a CIJ mixer. Charge ratios of 1:1 and 1:2 ecumicin: vitE succinate were tested, and both resulted in NPs ~70 nm in diameter and with a PDI <0.2. Encapsulation efficiency was measured as described above and was over 95%.

Ecumicin:vitE succinate was also encapsulated into NPs stabilized by specialized versions of PCL-PEG. These include PCL-PEG with an alexafluor fluorescent tag conjugated onto the end of the PEG chain, and PCL-PEG with hexamannose conjugated onto the end of the PEG chain. These formulations can be used for in vitro tracking, macrophage uptake, and targeting, e.g., organ targeting, tests, in addition to other uses of controlled delivery.

Ecumicin NPs have also been flash frozen and lyophilized. Dry powders produced this way were then redispersed back to nano-size upon water addition.

Example 7: Nanoparticles Encapsulating OZ439 with an Ion Pair Agent

OZ439 (artefenomel) is a synthetic trioxolane small molecule antimalarial having a molecular weight of 470 Da. It is promising as a single-dose oral cure for malaria. OZ439 has intermediate solubility and is not sufficiently hydrophobic to precipitate into nanoparticles. It was successfully encapsulated in NPs after being ion paired with sodium oleate. The stabilizer used was hydroxypropyl methylcellulose acetate succinate (HPMCAS). Particles formed were 150 nm and had a PDI <0.2. OZ439 is an example of a charged small molecule of intermediate solubility (logP~4.6) that can be encapsulated by the ion pairing FNP approach. Furthermore, this experiment demonstrated that a stabilizer other than a block copolymer may be used to stabilize nanoparticles produced through the ion pairing FNP strategy.

OZ439 was encapsulated within HPMCAS nanoparticles by the ion pairing Flash NanoPrecipitation approach. OZ439 was loaded in an organic stream of 67/33 v/v % THF and MeOH along with HPMCAS and sodium oleate and impinged against a water stream in a CIJ mixer. Charge ratios of 1:1 and 1:2 OZ439: oleate were tested, and both resulted in NPs ~150 nm in diameter and with a PDI <0.2. Encapsulation efficiency was measured to be over 95%.

Example 8: Nanoparticles Encapsulating Ovalbumin with an Ion Pair Agent

Ovalbumin (OVA) is an anionic protein that was encapsulated in PCL-b-PEG NPs by the ion pairing Flash NanoPrecipitation strategy. Ovalbumin has 385 amino acid residues, its molecular weight is 43,000 Da, and its charge at physiological pH is −48. Because ovalbumin is anionic, quaternary ammonium surfactants were used as ion pairing agents. Ovalbumin encapsulation demonstrates that the ion pairing Flash NanoPrecipitation approach is not limited to peptides and small molecules, but is effective for larger proteins as well.

OVA was encapsulated in nanoparticles by the ion pairing Flash NanoPrecipitation approach. In brief, OVA was dissolved in water at 5 mg/mL. This stream was impinged against an organic stream of 50/50 v/v % THF and MeOH containing $PCL_{5k}$-b-$PEG_{5k}$ and a quaternary ammonium surfactant. When at least one charge equivalent of surfactant was included, OVA was successfully encapsulated into stable NPs ~150 nm in diameter and with a PDI <0.2.

Nanoparticles were successfully formed with each of the following quaternary ammonium surfactants: cetyl trimethylammonium bromide, tetraoctylammonium bromide, tetrakis(decyl)ammonium bromide, tetradodecylammonium bromide, tetrahexadecylammonium bromide, didodecyldimethylammonium bromide, dimethylditetradecylammonium bromide, dimethyldioctadecylammonium bromide, and dimethyldihexadecylammonium bromide. Other cationic surfactants may be used. OVA nanoparticles are potentially useful as vaccines and for other immunology studies.

Example 9: Nanoparticles Encapsulating Lysozyme with Ion Pair Agents

Lysozyme (LYZ) is a cationic protein that was encapsulated in PCL-b-PEG NPs by the ion pairing Flash NanoPrecipitation strategy. Lysozyme has 129 amino acid residues, its molecular weight is 14,300 Da, and its charge at physiological pH is +8. Taken together, LYZ and OVA encapsulation demonstrate that the ion pairing Flash NanoPrecipitation approach is a robust approach that may be applied to both cationic and anionic proteins. LYZ was shown to still be an active protein after it is released from NPs.

LYZ was encapsulated in nanoparticles by the in situ ion-pairing Flash NanoPrecipitation (FNP) approach. LYZ was dissolved in water at 5 mg/mL. This stream was impinged against an organic stream of 50/50 v/v % THF and MeOH containing $PCL_{5k}$-b-$PEG_{5k}$ and a counterion such as sodium oleate.

The pre-forming approach was also used, with the counterions sodium dodecyl sulfate (SDS) and dextran sulfate (DXS). IP and LYZ were mixed in water; the resulting complex was dried by lyophilization and then resuspended in a mixture of THF and DMSO. This organic solution was mixed with a THF solution containing PCL5k-b-PEG5k block copolymer to create the organic feed stream for FNP. LYZ was successfully encapsulated into stable NPs ~150 nm in diameter and with a PDI <0.2.

In a modified pre-forming method, IP and LYZ were mixed in water. The resulting complex was centrifuged to pelletize the insoluble complex; the supernatant was removed; the pellet was then dried by lyophilization; and the pellet was then resuspended in a mixture of THF and dimethylsulfoxide (DMSO). This organic solution was then mixed with a THF solution containing PCL5k-b-PEG5k block copolymer to create the organic feed stream for Flash NanoPrecipitation (FNP).

Results for forming lysozyme-encapsulated NPs by HIP-FNP using each of the in situ, pre-formed, and modified pre-formed methods are shown in Table 5.

TABLE 5

Properties of lysozyme-encapsulated NPs fabricated by HIP-FNP

| Formulation | HIP-FNP Method | Size (nm) | PDI | Loading (%)* | Zeta (mV) |
|---|---|---|---|---|---|
| 1:1 Lys:SDS | Pre-formed | 56 ± 2 | 0.396 ± 0.063 | 42.7 | −6.3 ± 5.4 |
| 1:2 Lys:SDS | Pre-formed | 92 ± 1 | 0.191 ± 0.018 | 37.2 | −7.8 ± 4.1 |
| 1:4 Lys:SDS | Pre-formed | 119 ± 2 | 0.091 ± 0.048 | 29.7 | −9.3 ± 4.8 |
| 1:1 Lys:OA | In situ | 112 ± 1 | 0.129 ± 0.012 | 46.5 | −1.6 ± 11 |
| 1:2 Lys:OA | In situ | 126 ± 13 | 0.191 ± 0.026 | 43.5 | −6.2 ± 9.0 |
| 1:4 Lys:OA | In situ | 161 ± 3 | 0.224 ± 0.024 | 38.5 | −28.5 ± 7.0 |
| 1:1 Lys:DXS | Modified pre-formed | 52 ± 3 | 0.332 ± 0.044 | 44.8 | −7.2 ± 8.2 |
| 1:2 Lys:DXS | Modified pre-formed | 110 ± 1 | 0.171 ± 0.001 | 40.5 | −7.0 ± 5.0 |
| 1:4 Lys:DXS | Modified pre-formed | 62 ± 1 | 0.216 ± 0.012 | 34.0 | −10.5 ± 7.3 |

*Theoretical mass loading of lysozyme in NP, i.e. $mass_{lys}/mass_{NP}$

LYZ encapsulation efficiency was measured to be >90%. LYZ release from NPs was measured and found to depend on counterion and charge ratio in a manner consistent with the original findings for polymyxin, above.

NPs assembled using SDS as an ion pairing agent for LYZ released 50% of LYZ by 14 days at a 1:1 charge ratio. Release was slower for higher LYZ:SDS charge ratios. NPs assembled using OA as an ion pairing agent for LYZ released 30% of LYZ by 14 days at a 1:1 charge ratio. At a 1:2 charge ratio, 20% was released by 14 days, and at a 1:4 charge ratio, 10% was released by 14 days. Thus, (1) for a given counterion, LYZ release was slower at higher charge ratios; and (2) at the same charge ratio, LYZ paired with OA released more slowly than LYZ paired with SDS.

The activity of lysozyme, measured by its ability to lyse cells, was measured after release. Following release, up to 100% of released LYZ demonstrated activity equal to LYZ that was never encapsulated.

When paired 1:1 or 1:2 with OA, and when paired 1:1 with DXS, 100% of released LYZ was bioactive. When paired 1:4 with OA, and when paired 1:2 or 1:4 with DXS, and when paired 1:1 with SDS, approximately 60% of released LYZ was bioactive. When paired 1:2 or 1:4 with SDS, little (<10%) of released LYZ was bioactive.

These results show that the ion pairing Flash NanoPrecipitation approach may be used to encapsulate proteins without causing them to denature.

Embodiments according to the present invention may be useful in the treatment of infectious diseases, such as bacterial, fungal, viral, and parasitic infections, and the delivery of nucleic acids for gene therapy, gene delivery, or gene editing. For example, the controlled delivery of active therapeutic ingredients (APIs) through nanocarriers can result in improved bioavailability, reduced toxicity, sustained activity, simplified dosing regimens, improved patient adherence, and enhanced overall efficacy. For example, embodiments according to the present invention may be useful in controlled release, targeting to tumors, tissues, organs, regions of the GI tract, endosomes, or other areas of the body or of cells. Embodiments according to the present invention may be useful in encapsulating charged hydrophilic small molecules, peptides, proteins, and nucleic acids.

The invention includes methods for transiently changing API water solubility to enable API processing with nanoprecipitation methods. Without being bound by theory, a theoretical framework for optimizing processing conditions is presented herein. The rules for ion pair selection for nanoparticle stability are based on the hydrophobicity and the $pK_a$ of the IP. There are two processing routes. As a first route, the IP: API complex can be pre-formed and isolated as a single component and then assembled into NCs via Flash NanoPrecipitation. As a second route, the IP: API complex can be formed in a precipitation where the hydrophobic IP agent, the stabilizing polymer, and the hydrophilic API can be assembled into the final NC during a single precipitation step. The former (first) route has the advantage of knowing the stoichiometry of the IP: API a priori; the latter (second) route has the advantage of being a simple, single precipitation.

Hydrophilic APIs using Flash NanoPrecipitation can be encapsulated via hydrophobic ion pairing. For example, the following APIs can be encapsulated: antimicrobial small molecules OZ439, cinnarizine, clozapine, α-lipoic acid; peptides polymyxin B, colistin, mastoparan 7, mastoparan 17, sub5, LL37, ecumicin, streptomycin; proteins ovalbumin and lysozyme; aminoglycoside gentamycin; and nucleic acids such as linear salmon testes DNA or coiled plasmid DNA.

Nanoprecipitation-based methods can formulate active pharmaceutical ingredients (APIs) in a scalable and continuous manner with high API loading.

The ion pairing approach presented herein provides a powerful new tool for the encapsulation of API's.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A set of nanoparticles, comprising:
nanoparticles comprising
a modified salt comprising an active pharmaceutical ingredient (API) ion paired with a hydrophobic counterion; and
a nanoparticle encapsulant material substantially surrounding the modified salt,
wherein the nanoparticle encapsulant material comprises polycaprolactone-block-polyethylene glycol block copolymer (PCL-b-PEG),
wherein the active pharmaceutical ingredient (API) is a water-soluble linear cationic peptide of a molecular weight of from 1,422 Da to 2,000 Da and of at least 14% basic amino acids of amino acids,
wherein the hydrophobic counterion is an alkyl sulfate, and
wherein the set of nanoparticles has a Z-average diameter of at least 120 nm.

2. The set of nanoparticles according to claim 1, wherein the API is selected from the group consisting of mastoparan 7 (amino acid sequence INLKALAALAKALL-NH$_2$ [SEQ ID NO: 1), Sub5 (amino acid sequence RRWKIVVIRWRR-NH$_2$ [SEQ ID NO: 2]), LL37 (amino acid sequence FKRIVQRIKDFLR [SEQ ID NO: 3]), and combinations thereof.

3. The set of nanoparticles according to claim 1, wherein the hydrophobic counterion has a logP value of greater than

```
                          SEQUENCE LISTING

<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: mastoparan 7 (MP7)

<400> SEQUENCE: 1

Ile Asn Leu Lys Ala Leu Ala Ala Leu Ala Lys Ala Leu Leu
                5                   10

<210> SEQ ID NO 2
<211> LENGTH: 12
<212> TYPE: PRT
<213> ORGANISM: Artificial Sequence
<220> FEATURE:
<223> OTHER INFORMATION: sub5

<400> SEQUENCE: 2

Arg Arg Trp Lys Ile Val Val Ile Arg Trp Arg Arg
                5                   10

<210> SEQ ID NO 3
<211> LENGTH: 13
<212> TYPE: PRT
<213> ORGANISM: Artificial Sequence
<220> FEATURE:
<223> OTHER INFORMATION: LL37

<400> SEQUENCE: 3

Phe Lys Arg Ile Val Gln Arg Ile Lys Asp Phe Leu Arg
                5                   10
```

5 at a pH of 7 and wherein the release profile of the API displays a plateau in the release rate with time.

4. The set of nanoparticles according to claim 1, wherein the hydrophobic counterion is selected from the group consisting of dodecyl sulfate, decyl sulfate and combinations thereof.

5. The set of nanoparticles according to claim 1,
wherein the API is selected from the group consisting of mastoparan 7 (amino acid sequence INLKA-LAALAKALL-$NH_2$ [SEQ ID NO: 1), Sub5 (amino acid sequence RRWKIVVIRWRR-$NH_2$ [SEQ ID NO: 2]), LL37 (amino acid sequence FKRIVQRIKDFLR [SEQ ID NO: 3]), and combinations thereof, and
wherein the hydrophobic counterion is dodecyl sulfate.

6. The set of nanoparticles according to claim 1, wherein the API is mastoparan 7 (amino acid sequence INLKA-LAALAKALL-$NH_2$ [SEQ ID NO: 1]).

7. The set of nanoparticles according to claim 1, wherein the API is Sub5 (amino acid sequence RRWKIVVIRWRR-$NH_2$ [SEQ ID NO: 2]).

8. The set of nanoparticles according to claim 1, wherein the API is LL37 (amino acid sequence FKRIVQRIKDFLR [SEQ ID NO: 3]).

9. The set of nanoparticles according to claim 1, wherein the hydrophobic counterion is dodecyl sulfate.

10. The set of nanoparticles according to claim 1, wherein the hydrophobic counterion is decyl sulfate.

11. A method for producing the set of nanoparticles according to claim 1, comprising:
providing the active pharmaceutical ingredient (API),
providing an ion-pairing (IP) reagent which comprises a hydrophobic counterion wherein said hydrophobic counter-ion is an alkyl sulfate,
mixing the API and IP reagent in water to from a water-insoluble precipitate of the API and hydrophobic counterion;
removing the water;
dissolving the water-insoluble precipitate into an organic solvent to form an organic solution comprising the API and hydrophobic counterion together;
combining the organic solution comprising the API and hydrophobic counterion together with polycaprolactone-block-polyethylene glycol (PCL-b-PEG); and
combining the organic solution comprising the API, the hydrophobic counterion, and the PCL-b-PEG with a polar solvent to form nanoparticles via precipitation.

12. The method according to claim 11, wherein
the polar solvent is water.

13. The method according to claim 12, wherein the combining of the organic solution comprising the API, the hydrophobic counterion, and the PCL-b-PEG with water as the polar solvent is by continuous mixing.

14. A method for producing the set of nanoparticles according to claim 1, comprising:
providing the active pharmaceutical ingredient (API);
providing an ion-pairing (IP) reagent which comprises a hydrophobic counterion wherein the hydrophobic counterion is an alkyl sulfate;
dissolving the API in a polar solvent to form a polar solution comprising the API;
dissolving the IP reagent and polycaprolactone-block-polyethylene glycol (PCL-b-PEG) in an organic solvent to form an organic solution comprising the hydrophobic counterion and the PCL-b-PEG; and
combining the polar solution comprising the API with the organic solution comprising the hydrophobic counterion and the PCL-b-PEG to form the nanoparticles via precipitation.

15. The method according to claim 14,
wherein the combining of the polar solution comprising the API with the organic solution comprising the hydrophobic counterion and the PCL-b-PEG is by continuous mixing and
wherein the organic solvent is less polar than the polar solvent.

16. The method according to claim 15,
wherein the organic solvent is water-miscible and
wherein the polar solvent is water.

* * * * *